United States Patent [19]
Ivey et al.

[11] Patent Number: 5,976,580
[45] Date of Patent: *Nov. 2, 1999

[54] NUTRIENT FORMULATION AND PROCESS FOR ENHANCING THE HEALTH, LIVABILITY, CUMULATIVE WEIGHT GAIN OR FEED EFFICIENCY IN POULTRY AND OTHER ANIMALS

[75] Inventors: Francis J. Ivey, Creve Coeur; Julia J. Dibner, Chesterfield; Christopher D. Knight, St. Louis, all of Mo.

[73] Assignee: Novus International, Inc., St. Louis, Mo.

[*] Notice: This patent is subject to a terminal disclaimer.

[21] Appl. No.: 08/760,881

[22] Filed: Dec. 6, 1996

Related U.S. Application Data

[63] Continuation-in-part of application No. 08/647,719, May 24, 1996, which is a continuation-in-part of application No. 08/597,815, Feb. 7, 1996, abandoned, which is a continuation-in-part of application No. 08/483,297, Jun. 7, 1995.

[51] Int. Cl.$^6$ ........................................ A23K 1/18
[52] U.S. Cl. ............................ 426/2; 426/60; 426/250; 426/807
[58] Field of Search ........................ 426/2, 807, 60, 426/250

[56] References Cited

U.S. PATENT DOCUMENTS

| | | |
|---|---|---|
| 1,867,063 | 7/1932 | Dawe . |
| 2,593,577 | 4/1952 | Lewis ............................................. 99/4 |
| 2,620,274 | 12/1952 | Lewis et al. .................................... 99/4 |
| 2,946,722 | 7/1960 | Hoffman et al. ......................... 167/53.1 |
| 3,635,723 | 1/1972 | Shelton et al. .............................. 99/131 |
| 4,089,979 | 5/1978 | Jackson ....................................... 426/69 |
| 4,143,171 | 3/1979 | Buckley et al. .......................... 426/331 |
| 4,158,706 | 6/1979 | Ernst et al. ............................... 426/327 |
| 4,495,208 | 1/1985 | Friedman et al. ....................... 426/335 |
| 4,910,024 | 3/1990 | Pratt ............................................ 126/2 |
| 4,988,531 | 1/1991 | Moore et al. ............................. 426/578 |
| 5,089,277 | 2/1992 | Prochnow .................................... 426/1 |
| 5,139,792 | 8/1992 | Ware et al. .................................. 426/2 |
| 5,217,740 | 6/1993 | Lanter ....................................... 426/573 |
| 5,387,522 | 2/1995 | Vasington et al. ....................... 435/287 |
| 5,514,408 | 5/1996 | Lan et al. ................................. 426/656 |
| 5,603,980 | 2/1997 | Bussiere et al. ......................... 426/641 |

FOREIGN PATENT DOCUMENTS

| | | |
|---|---|---|
| 1249516 | 1/1989 | Canada . |
| 158075 | 10/1985 | European Pat. Off. . |
| 243548 A1 | 11/1987 | European Pat. Off. . |
| 00287699A3 | 10/1988 | European Pat. Off. . |
| 285441 A2 | 10/1988 | European Pat. Off. . |
| 592220 A2 | 4/1994 | European Pat. Off. . |
| 0749695A1 | 12/1996 | European Pat. Off. . |
| 2031748 | 4/1980 | United Kingdom . |
| 2055034 | 2/1981 | United Kingdom . |
| WO93/00017 | 1/1993 | WIPO . |
| WO 95/16461 | 6/1995 | WIPO . |
| WO 96/12413 | 5/1996 | WIPO . |
| WO96/27666 | 9/1996 | WIPO . |
| WO96/39862 | 12/1996 | WIPO . |

OTHER PUBLICATIONS

Thorne et al., "Automated High Moisture Diet Feeding System for Laying Hens", Poultry Science 68(8):1114–1117 (1989).

Tadttyanant et al., "Influence of Wet and Dry Feed on Laying Hens Under Heat Stress", Poultry Science 70(1):44–52 (1991).

Dalynn Laboratory Product, Information Sheet (no date).

(List continued on next page.)

*Primary Examiner*—Helen Pratt
*Attorney, Agent, or Firm*—Senniger, Powers, Leavitt & Roedel

[57] ABSTRACT

A nutrient formulation including moisture, a coloring agent, a palatability modifier, and/or an adjuvant which is designed for use in poultry and other animals, and a method of feeding it which improves subsequent livability, cumulative feed efficiency, weight gain, and resistance to disease challenge or other stresses is disclosed.

40 Claims, 9 Drawing Sheets

OTHER PUBLICATIONS

Gary Thornton "A Novel Cocci Vaccine System", Broiler Industry, May 1997, pp. 36, 38, 40.

"Cocci Control By Vaccine", From a talk by Dr. Eng Hong Lee at the 1991 Saskatchewan Poultry Industry Conference, Canada Poultryman, Sep. 1991, p. 39.

Baranyiova "Influence of Deutectomy, Food Intake And Fasting On The Digestive Tract Dimensions In Chickens After Hatching" Acta Vet. Brno, vol. 41 (1972) pp. 373–384.

Baranyiova et al. "Morphological Changes In The Intestinal Wall In Fed And Fasted Chickens In The First Week After Hatching", Acta Vet. Brno, vol. 45 (1976) pp. 151–158.

Buddington et al., "Ontogenetic Development of Intestinal Nutrient Transporters" Annu. Rev. Physiol., vol. 51 (1989) pp. 601–619.

Casteel et al. "The Influence of Extended Posthatch Holding Time and Placement Density on Broiler Performance" vol. 73. (1994) pp. 1679–1684.

Chamblee et al. "Yolk Sac Absorption and Initiation of Growth in Broilers" Poultry Science, vol. 71 (1992) pp. 1811–1816.

Engku Azahan et al. "Growth, Food Intake and Energy Balance of Layer and Broiler Chickens Offered Glucose in the Drinking Water and the Effect of Dietary Protein Content" British Poultry Science, vol. 30 (1989) pp. 907–917.

Entenman et al. "The Lipid Content of Blood, Liver, and Yolk Sac of the Newly Hatched Chick and the Changes That Occur in These tissues During the First Month of Life" J. Biol. Chem. vol. 133 (1940) pp. 231–241.

Fanguy et al. "Effect of Delayed Placement on Mortality and Growth Performance of Commercial Broilers" Poultry Science, vol. 59 (1980) pp. 1215–1220.

Fedde et al. "Factors Affecting the Absorbability of Certain Dietary Fats in the Chick" J. Nutrition, vol. 70, (1960) pp. 447–452.

Gomez et al. "The Use of Bile Salts to Improve Absorption of Tallow in Chicks, One to Three Weeks of Age" Poultry Science vol. 55 (1976) pp. 2189–2195.

Hager et al. "Posthatch Incubation Time and Early Growth of Broiler Chickens" Poultry Science, vol. 62 (1983) pp. 247–254.

Kienholz et al. "Oral Food Slurry Injection For Newly Hatched Poults" Poultry Science, vol. 49 (1970) pp. 678–680.

Kingston, D. "Some Hatchery Factors Involved in Early Chick Mortality" Australian Veterinary Journal, vol. 55 (Sep. 1979) pp. 418–421.

Knoblock et al. "Ingestive Behavior of Day–Old Chicks" Poultry Science, vol. 49 (1970) pp. 598–599.

Krogdahl et al. "Influence of Age on Lipase, Amylase, and Protease Activities in Pancreatic Tissue and Intestinal Contents of Young Turkeys" Poultry Science, vol. 68, pp. 1561–1568.

Moran, E. "Effects of Egg Weight, Glucose Administration at Hatch, and Delayed Access to Feed and Water on the Poult at 2 Weeks of Age" Poultry Science, No. 69 (1990) pp. 1718–1723.

Moran Jr., "Subcutaneous glucose Is More Advantageous In Establishing The Posthatch Poult Than Oral Administration" Poultry Science, vol. 67 (1988) pp. 493–501.

Moran Jr., "Effects of Posthatch Glucose on Poults Fed and Fasted During Yolk Sac Depletion" Poultry Science, vol. 68 (1989) pp. 1141–1147.

Moreto et al. "Transport of L–proline and $\alpha$–methyl–D–glucoside by chicken Proximal Cecum During Development" Am. J. Physiol. vol. 260 (1991) pp. G457–G463.

Nitsan et al. "Organ Growth and Digestive Enzyme Levels to Fifteen Days of Age in Lines of Chickens Differing in Body Weight" Poultry Science, vol. 70 (1991) pp. 2040–2048.

Nitsan et al. "Growth and Development of The Digestive Orgnas And Some Enzymes in Broiler Chickens After Hatching" British Poultry Science, vol. 32 (1991) pp. 515–523.

Novle et al. "Lipid changes in the Residual Yolk and Liver of Chick Immediately After hatching" Biol Neonate, vol. 56 (1989) pp. 228–236.

Noy et al. "Digestion and Absorption in the Young Chick" Poultry Science, vol. 74 (1995) pp. 336–373.

Phelps et al. "Research Note: Effect of Prefeeding on Physiological Parameters Associaed with Turkey Poulttl Mortality" Poultry Science, vol. 66 (1987) pp. 1882–1884.

Phelps et al. "The Posthatch Physiology of the Turkey Poult–III. Yolk Depletion and Serum Metabolites" Comp. Biochem. Physiol., vol. 87A, No. 2 (1987) pp. 409–415.

Pinchasov et al. "Comparison of Post–Hatch Holding Time and Subsequent Early Performance of Broiler Chicks and Turkey Poults" British Poultry Science, vol. 34 (1993) pp. 111–120.

Pinchasov et al. "A Single Post–Hatch Intubation of Various Nutrients Improves Subsequent Early Performance of Young Birds" Proceedings: XIX World's Poultry Congress, vol. 3 (1992) pp. 614–618.

Polin et al. "The Effect of Bile Acids and Lipase on Absorption of Tallow in Young Chicks" Poultry Science, vol. 59 (1980) pp. 2738–2743.

Sell et al. "Influence of Age on Utilization of Supplemental Fats by Young Turkeys" Poultry Science, vol. 56 (1986) pp. 546–554.

Sell, J. "Intestinal Disaccharidases of Young Turkesy: Temporal Development and Influence of Diet Composition" Poultry Science, vol. 68 (1989) pp. 265–277.

Sell et al. "Developmental Patterns of Selected Characteristics of the Gastrointestinal Tract of Young Turkeys" Poultry Science, vol. 70 (1991) pp. 1200–1205.

Shehata et al. "Development of Brush–border Membrane Hexose Transport System in Chick Jejunum" Am. J. Physiol. vol. 240 (1981) pp. G102–108.

Taylor, Gib. "Ways to improve hatchability one percent improve profits" Poultry Digest, (Sep. 1995) pp. 20–26.

Thaxton et al. "Growth, Efficiency, and Livability of Newly Hatched Broilers as Influenced by Hydration and Intake of Sucrose" Poultry Science, vol. 55 (1976) pp. 2275–2279.

Twining, Jr. et al. "Feed and Water Management of the Broiler Chick for the First 72 Hours" Poultry Science, vol. 57 (1978) pp. 1325–1328.

Vanheel et al. "Resorption of Yolk Lipids by the Pigeon Embryo" Comp. Biochem. Physiol., vol. 68A (1981) pp. 641–646.

Waldroup et al. "The Effectiveness of Nutrient Solutions Given to Young Turkey Poults in Drinking Water or by Oral and Parenteral Dosage" Poultry Science, vol. 53 (1974) pp. 1056–1060.

Warriss et al. "Responses of Newly Hatched Chicks to Inanition" Vetrinary Record, vol. 130 (1991) pp. 49–53.

Wyatt et al. "Influence of Egg Size, Eggshell Quality, and Posthatch Holding time on Broiler Performance" Poultry Science, vol. 64 (1985) pp. 2049–2055.

Wyatt et al. "Influence of Hatcher Holding Times on Several Physiological Parameters Associated With the Immune System of Chickens" Poultry Science., vol. 65 (1986) pp. 2156–2164.

Tadtiyanant, C., Lyons, J J., Vandepopuliere, J.M., "Influence of Wet and Dry Feed on Laying Hens Under Heat Stress", Poultry Science, vol. 70, No. 1, (1991) pp. 44–52.

Thorne, D.H., Vandepopuliere, J.M. and Lyons, J.J., "Automated High Moisture Diet Feeding System for Laying Hens," Poultry Science vol. 68, No. 8 (1989), pp. 1114–1117.

EFFECT OF FORMULATION ON DAY 7, 14 AND 21 CUMMULATIVE MORTALITY IN POULTS a,b P<05

AMOUNT OF IgA IN THE BILE (DAY 21) OF BIRDS GIVEN 1027 WITH OR WITHOUT IMMUNOMODULATORS FOR THE FIRST TWO DAYS OF LIFE a,b P<05

GAIN AND CUMULATIVE FEED TO GAIN OF BIRDS GIVEN 1027 WITH OR WITHOUT VITAMINS A AND E (1027 AE) AND CHALLENGED WITH COCCIDIA ON DAY 15 a,b,c,y,z P<05

FEED TO GAIN AND CUMULATIVE LIABILITY OF BIRDS GIVEN 1027 WITH OR WITHOUT CON A AND LEVAMISOLE (1027CL) AND CHALLENGED WITH COCCIDIA ON DAY 14 a,b,y,z P<05

CONSUMPTION OF COLORED AND TEXTURED 1027 BY HATCHING TURKEYS

NUTRIENT FORMULATION AND PROCESS FOR ENHANCING THE HEALTH, LIVABILITY, CUMULATIVE WEIGHT GAIN OR FEED EFFICIENCY IN POULTRY AND OTHER ANIMALS

This application is a continuation-in-part of U.S. application Ser. No. 08/647,719, filed May 24, 1996, which is a continuation-in-part of U.S. application Ser. No. 08/597,815, filed Feb. 7, 1996, now abandoned which is a continuation-in-part of U.S. application Ser. No. 08/483,297, filed Jun. 7, 1995, the entire contents of which are herein incorporated by reference.

BACKGROUND OF THE INVENTION

The present invention is directed to a high moisture material for providing nutrients, drugs, vitamins, minerals, bile salts, surfactants, probiotics, enzymes, peptides, hormones, prostaglandins, antioxidants, living cells, and immunoactive agents to poultry and other animals, and more particularly, a high moisture material and process which may be used to improve the health and enhance the livability, cumulative weight gain and feed conversion efficiency of poultry and other animals.

For economic reasons, the management of chick hatching in commercial facilities places high importance on percent chicks hatched of eggs set. To achieve hatch rates of 90%, early-hatching birds are often left in the hatch incubator for a period of time to allow the later-hatching chicks to emerge and dry. By the time the chicks are removed from the incubator tray, therefore, they will range in age from several hours up to about 2 days in age (as measured from hatching for each bird). This period is referred to as the post-hatch holding period.

After the chicks are removed from the incubator trays in a commercial hatchery, they are processed (inoculated and sexed) and then placed in boxes commonly referred to as chick boxes for shipping to the production farm. The processing period typically requires several hours and the chicks may reside in the chick boxes for several more hours before transit to the production farm actually begins.

Commercial hatcheries for poultry typically provide chicks for a number of production farms, often over a wide geographical area. Typically, feed and water are not provided until the birds reach the production farm and, as a result, the birds may go several days before feed and water are provided. The presence of the lipid-rich residual yolk sac and reserves of lipid in the liver, however, ensure that the minimal nutritional needs of hatchling birds are met (Freeman et al., *Development of the Avian Embryo*, London, Chapman and Hall, 1974). Thus, a period of inanition after hatching is normal in birds and does not necessarily threaten their survival (Entenman et al., *The Lipid Content of Blood, Liver, and Yolk Sac of the Newly Hatched Chick and the Changes That Occur in These Tissues During the First Month of Life*, J. Biol Chem., Vol. 133, pp. 231–241 (1940); Vanheel et al., *Resorption of Yolk Lipids by the Pigeon Embryo*, Comp. Biochem. Physiol., Vol. 68A pp. 641–646 (1981); Phelps et al., *The Posthatch Physiology of the Turkey Poult-III. Yolk Depletion and Serum Metabolites*, Comp. Biochem. Physiol., Vol. 87A, No. 2 pp. 409–415 (1987); Noble et al., *Lipid Changes in the Residual Yolk and Liver of the Chick Immediately after Hatching*, Biol Neonate, Vol. 56, pp. 228–236 (1989); Chamblee et al, *Yolk Sac Absorption and Initiation of Growth in Broilers*, Poultry Science, Vol. 72, pp. 1811–1816 (1992)). This does not mean, however, that using yolk residue as the single nutrient source in hatchlings will provide optimum subsequent livability, disease resistance, or gain and feed efficiency. The delayed placement has been shown to reduce subsequent livability (Kingston, *Some Hatchery Factors Involved in Early Chick Mortality*, Australian Veterinary Jour., Vol. 55, pp. 418–421 (1979); Fanguy et al., *Effect of Delayed Placement on Mortality and Growth Performance of Commercial Broilers*, Poultry Science, Vol. 59, pp. 1215–1220 (1980)), disease resistance (Wyatt et al., *Influence of Hatcher Holding Times on Several Physiological Parameters Associated With the Immune System of Chickens*, Poultry Science, Vol. 65, pp. 2156–2164 (1986); Casteel et al., *The Influence of Extended Posthatch Holding Time and Placement Density on Broiler Performance*, Poultry Science, Vol. 73, pp. 1679–1684 (1994)) and growth performance (Hager et al., *Education and Production Posthatch Incubation Time and Early Growth of Broiler Chickens*, Poultry Science, Vol. 62, pp. 247–254 (1983); Wyatt et al., *Influence of Egg Size, Eggshell Quality, and Posthatch Holding Time on Broiler Performance*, Poultry Science, Vol. 64, pp. 2049–2055 (1985); Pinchasov et al., *Comparison of Post-Hatch Holding Time and Subsequent Early Performance of Broiler Chicks and Turkey Poults*, British Poultry Science, Vol. 34, pp. 111–120 (1993)). Provision of individual nutrients such as glucose has not been found to consistently or permanently improve performance or livability when administered as a simple solution in the absence of other nutrients (Azahan et al., *Growth, Food Intake and Energy Balance of Layer and Broiler Chickens Offered Glucose in the Drinking Water and the Effect of Dietary Protein Content*, British Poultry Science, Vol. 30, pp. 907–917 (1989); Moran, *Effects of Posthatch Glucose on Poults Fed and Fasted During Yolk Sac Depletion*, Poultry Science, Vol. 68, pp. 1141–1147 (1989); Moran *Effects of Egg Weight, Glucose Administration at Hatch, and Delayed Access to Feed and Water on the Poult at 2 Weeks of Age*, Poultry Science, Vol. 69, pp. 1718–1723 (1990)).

Although provision of water and feed can result in performance superior to that of fasted, water-deprived birds, attempts to include water in the hatch incubator or in transport boxes have been unsuccessful. This is because humidity control and relatively high temperature are critical in ensuring high hatchability and because water alone or in a simple gruel can escape, resulting in some chicks getting wet. Chicks cannot regulate their body temperature sufficiently well to tolerate cooling by evaporation. Since inanition does not threaten survival, commercial practice is not to offer feed or water until the animals reach the farm.

SUMMARY OF THE INVENTION

Among the objects of the invention, therefore, may be noted the provision of a high moisture material to improve the health and enhance the livability, cumulative weight gain and feed conversion efficiency of poultry and other animals. The formulation may be fed, for example, immediately after hatching or birth of the animal and for this application, the formulation preferably excludes nutrients which are not used well during the first days of life and provides those which are readily used and confer a performance advantage. Also among the objects of the invention is a formulation which is stabilized against microbial growth, is resistant to syneresis and which can be packaged in bulk, shipped, extruded (with or without prior remixing of the bulk material) and divided into dosage unit form at the location of use of the formulation.

Briefly, therefore, the present invention is directed to a process for enhancing the health, livability, cumulative weight gain or feed conversion efficiency of poultry. The process comprises feeding the hatchlings a high moisture material before they are started on a diet comprising dry food. The hatchlings are fed the high moisture material beginning at a point in time preferably within the first 5 days of hatching, more preferably within the first 3 days of hatching. The high moisture material can contain a coloring agent, palatability modifier, or adjuvant. Whether an adjuvant is present or not, the high moisture material also enhances weight gain as well as resistance to disease challenge or other stresses in poultry.

The present invention is also directed to a composition and process for inoculating poultry and other animals with living cells such as yeast or bacteria. The animal is fed a high moisture material which contains a number of colony forming units of the cells which is sufficient to inoculate the animal and produce the desired effect.

The present invention is also directed to high moisture materials for enhancing the health, livability, cumulative weight gain or feed conversion efficiency of poultry. These high moisture materials contain at least about 50% by weight water, at least about 10% by weight digestible carbohydrate and, optionally, one or more additional ingredients selected from the group consisting of bile salts, surfactants, enzymes, enzyme co-factors, hormones, prostaglandins, peptides, immunoglobulins, cytokines, vaccines and other immunomodulators, antioxidants, amino acids, sources of amino acids and amino acid analogs, antibiotics, vitamins and minerals. The high moisture material is preferably prepared in bulk, extruded and divided into dosage unit form at the site where the high moisture material is fed to the animal.

Other objects and features of the invention will be in part apparent and in part pointed out hereinafter.

DETAILED DESCRIPTION OF THE INVENTION

Figure 1:
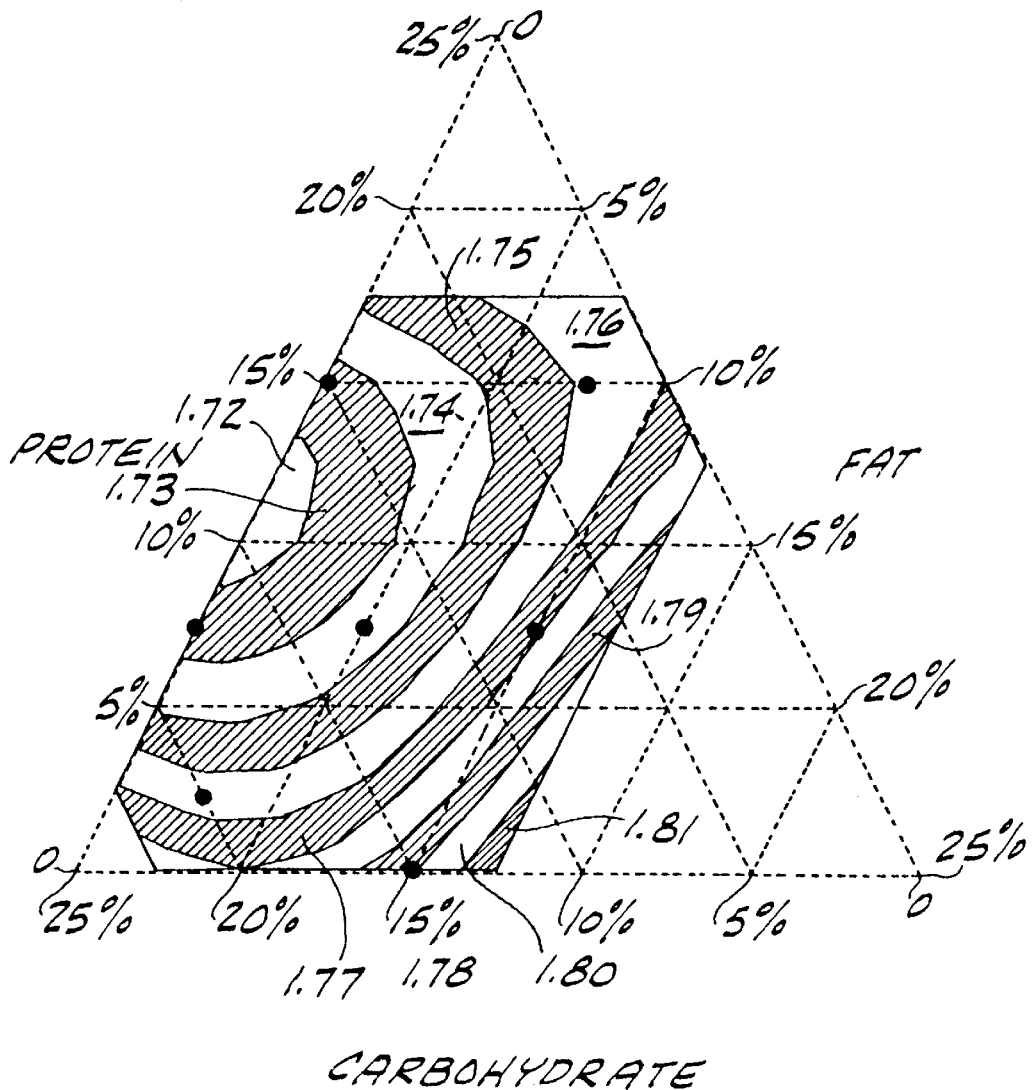
FIG. 1 is a graph depicting the results of Example 12.

Surprisingly, it has been discovered that the growth of poultry can be stimulated, the livability, cumulative weight gain and feed conversion efficiency of the poultry can be improved by feeding to poultry a formulation of the present invention which is referred to herein as a high moisture material. As used herein, the term high moisture material means a colloid in which the dispersed phase (starch, gum or protein) has combined with the continuous phase (water) to produce a viscous, dough-like gel in which larger particles (e.g., particles greater than 5 μm in size) such as soy, corn or rice may be suspended.

In one embodiment of the present invention, the high moisture material is first fed to poultry hatchlings which are within five, four, three, two or even one day of hatching (as determined for each bird). Preferably, the high moisture material is fed to the hatchlings before they are offered dry food or allowed to drink water ad libitum, and more preferably before they are offered dry food, at all. The high moisture material may be placed, for example, in the hatching incubator along with the eggs from which the poultry will hatch so that the high moisture material is available to the hatchlings immediately upon hatching. Providing the high moisture material to the chicks prior to their introduction to solid food reduces the likelihood that the hatchlings will suffer by consuming dry food without simultaneously drinking.

In another embodiment of the present invention, the high moisture material may be made available to the hatchlings prior to or during shipping by placing the high moisture material in the chick boxes along with the chicks. In accordance with this embodiment, it is preferred that the high moisture material be placed in the chick boxes before transit begins so that the chicks will have the opportunity to consume the high moisture material before they begin travelling (that is, moving by surface or air transportation from the site of the incubator to a remote location such as a poultry production farm which may be, for example, one or more miles away from the location of the incubator). The amount of high moisture material placed in the chick boxes need not be sufficient to enable the chicks to feed on it for the entire transit period.

In a further embodiment of the present invention, the high moisture material is fed to the poultry after they are shipped from the site where they are hatched to a remote location such as a poultry production farm or other intermediate facility. After being shipped, some chicks do not readily begin eating dry food and drinking water when it is offered. For such applications, it may be desirable to feed the transported poultry the high moisture material until the poultry begin eating dry food and drinking water ad libitum. In addition, the high moisture material may also be fed to the poultry at this time or even a later time to administer drugs or other substances as described herein.

Typically, chick boxes are filled to capacity with hatchling chicks, leaving little additional room for the high moisture material of the present invention. As a practical matter, therefore, hatchling chicks which are in the chick boxes along with the high moisture material will stand upon, brush against, peck at, and otherwise come into contact with the high moisture material. Because hatchling chicks cannot regulate their body temperature sufficiently well to tolerate evaporative cooling, it is important that the hatchlings not be wetted by (or become damp from) the high moisture material under these conditions. Necessarily, therefore, the high moisture material should be resistant to syneresis under these conditions, that is, the high moisture material should not release an amount of water which is sufficient to wet the floor of the container in which the hatchlings are being held or the hatchlings as a consequence of their standing upon it, brushing up against it, pecking at it, or otherwise coming into contact with it.

When the high moisture material is initially offered to the poultry or other animal, it should contain at least about 40% by weight water (an amount which is in excess of the amount of water contained in "dry" poultry feeds), preferably at least about 50% by weight water, more preferably between about 50% and about 85% by weight water, and most preferably between about 60% and about 80% by weight water, based upon the weight of the high moisture material. The non-aqueous fraction of the high moisture material is sometimes referred to herein as the "dry matter" or the "solid matter" fraction, with the two terms being used interchangeably.

Carbohydrates provide a source of nutrition for the animals and, in addition, can aid in the formation of the solid.

In general, digestible carbohydrates constitute at least about 8% by weight of the high moisture material, preferably at least about 10% by weight of the high moisture material and, for some applications, at least about 20% by weight of the high moisture material. The digestible carbohydrates contemplated herein include isolated carbohydrates such as corn starch, potato starch, wheat starch, rice starch, cellulose, pectin, agarose, and gums; bioavailable sugars such as glucose, fructose, and sucrose; chemically modified starches such as modified corn starch, methylcellulose, carboxymethylcellulose, and dextrin; humectants such as glycerol or propylene glycol; invert sugar; and ground complex carbohydrates such as corn, rice, oats, barley, wheat, sorghum, rye, millet, cassava, triticale and tapioca, in whole, ground, cracked, milled, rolled, extruded, pelleted, defatted, dehydrated, solvent extracted or other processed form. When included, modified starches preferably constitute at least about 0.01% by weight of the high moisture material.

The high moisture material is formed from a mixture of water and a combination of ingredients which enables the formation of a high moisture material from the mixture and which satisfies the nutrient specifications, if any. Depending upon the ingredients selected, preparation of the high moisture material may additionally require heating the mixture. In one embodiment, the mixture contains starch and is heated until the starch granules rupture and the mixture becomes viscous. See, for example, Lewis U.S. Pat. No. 2,593,577. In another embodiment, the high moisture material is formed from a colloidal solution containing a gum dissolved in water; some gums enable the formation of high moisture materials from the colloidal solution without heating whereas others require that the solution be heated to a temperature in excess of about 180° F. Generally, gums can constitute about 0.001% to about 5% by weight of the high moisture material. Gums which may be used for this purpose are generally high molecular weight molecules of plant or animal origin, usually with colloidal properties, which in appropriate solvents are able to produce gels, such as agar, algin and carrageenan derived from seaweeds, plant exudates such as gum arabic, ghatti and tragacanth, plant extracts such as pectin, plant seeds such as guar, locust bean, and animal exudates such as plasma, serum albumin, egg albumin, chitin and gelatin. Other gums include amylose and amylopectin and gums of bacterial origin. See, for example, U.S. Pat. No. 5,217,740. In yet another embodiment, a gelatinizing aid such as carboxymethylcellulose, lignin, or a lignin derivative is dissolved in water to form a colloidal solution which forms a gel upon cooling.

After the ingredients of the high moisture material are mixed and heated (if necessary), the material may be allowed to form a gel in situ, transferred to another vessel or container for storage in bulk form, or cast in a shape and size which enables convenient feeding to animals. In a preferred embodiment, the mixture may be transferred to a container such as a drum or a deformable plastic which holds, for example, between about 25 and about 1,000 kilograms of the high moisture material.

For administration to poultry hatchlings, the gelled high moisture material preferably has a texture which enables the hatchlings to break the high moisture material apart by pecking; that is, the high moisture material is sufficiently soft such that the pecking of the hatchlings will cause the high moisture material to break or crumble into consumable fragments. Once broken into fragments, however, the high moisture material preferably does not adhere to the feathers or down of poultry hatchlings. In addition, it is preferred that the high moisture material comprise particles which are visible to the naked eye. Such particles include, for example, ground ingredients such as ground grains and seeds such as corn and soy beans, and other particles which do not exceed the size of a typical grain of white rice (i.e., about 1 mm).

Unless the high moisture material will be promptly fed to an animal, it is preferably stabilized against microbial growth. That is, upon being sealed and stored at room temperature for a period of at least about eight weeks the stabilized high moisture material will show no indication of microbial growth. The high moisture material may be stabilized, for example, by sterilizing, adding a microbial growth inhibitor such as methyl paraben or a sorbate thereto, or adjusting the pH of the mixture from which the high moisture material is formed. Preferably, the high moisture material is stabilized by adjusting the pH of the mixture with an acid to a pH within the range of about 3 to about 4, more preferably to a pH within the range of about 3 to 3.5. Such acid can be a low molecular weight carboxylic acid, preferably having a chain length of $C_2$–$C_{10}$, more preferably having a chain length of $C_2$–$C_7$, most preferably having a chain length of $C_2$–$C_5$. Examples of useful carboxylic acids include citric acid, propionic acid, and fumaric acid. Phosphoric acid can also be used. Propionic acid can be present in an amount of from about 0.5% to about 1% by weight of the present high moisture material; citric acid and fumaric acid can be present in an amount of from about 0.7% to about 2% by weight of the high moisture material.

The high moisture material may be fed to the animals in a variety of manners. For example, the amount required for feeding may be scooped, sliced or otherwise removed from the unit, container or vessel in which it is held and transferred to the animal(s) in unit form. To reduce labor, however, the unit doses of the solid may be generated from the bulk material by pumping or compressing the high moisture material and forcing it through an opening. The resulting material, referred to herein as an extrudate, is in the form of a high moisture material containing substantially the same amount of water as the bulk material. In one embodiment, the high moisture material may be in a compressible container which is compressed to force the high moisture material to flow through a die and to a location where it can be consumed by the animal(s). In some instances it may be preferred to combine the high moisture material with a heat labile or other ingredient before the high moisture material is fed to the animal(s); in these instances, the heat labile ingredient is added to the high moisture material at or near room temperature and the total mixture is then remixed before being divided into unit doses. Alternatively, the heat labile material may be sprayed onto the unit dose of high moisture material. In any event, however, the extrusion step should not cause the high moisture material to lose a significant amount of water or the desired texture. That is, the extrudate should preferably contain at least 40% by weight water, preferably at least about 50% by weight water, more preferably between about 50% and about 85% by weight water, and most preferably between about 60% and about 80% by weight water, based upon the weight of the extrudate and, in addition, the extrudate should be sufficiently soft such that the pecking of the hatchlings will cause the high moisture material to break or crumble into consumable fragments.

The high moisture material of the present invention resists syneresis when it contains at least about 5% protein. To increase its nutritional value for some applications such as longer-term feeding, the high moisture material preferably comprises at least about 7% by weight, more preferably at least about 10% by weight, of an amino acid source such as protein(s), amino acids, precursors or analogues of amino acids, and mixtures thereof. In addition, it is preferred that the weight ratio of all digestible carbohydrate to all amino acid sources in the high moisture material be between about 0.6:1 and 3:1, respectively. Exemplary amino acids are essential amino acids such as methionine, tryptophan, threonine, arginine and lysine. Exemplary amino acid precursors are 2-hydroxy-4-(methylthio)butanoic acid sold, for example, under the trademark Alimet® by Novus International (St. Louis, Mo.), and salts of 2-hydroxy-4-(methylthio)butanoic acid such as the calcium and sodium salts. Exemplary proteins include single cell proteins or hydrolysates of proteins such as those from yeast, algae or bacteria; isolated animal proteins, peptides or hydrolysates of proteins such as hemoglobin, myosin, plasma, or other serum proteins, collagen, casein, albumin or keratin; complex protein sources or hydrolysates of proteins such as milk, blood, whey, blood meal, meatmeal, feathermeal, fishmeal, meat and bone meal, poultry offal, poultry by-product meal, hatchery by-products, egg offal, egg white, egg yolk, and eggs without shells; plant protein or hydrolysate of proteins such as soybean meal, isolated soybean protein, wheat protein, wheat germ, distillers grains and gluten.

Although not preferred for certain applications, fat may also be included in the high moisture material in relatively small proportions. A suitable high moisture material, therefore, would comprise at least about 50% by weight water and no more than about 5% by weight fat, preferably no more than about 4% by weight fat. Suitable fats include fatty acids such as linoleic acid; isolated plant oils such as sunflower, safflower, soybean, peanut, canola, corn, rapeseed, olive, linseed and palmkernal; fat meals such as cottonseed, peanut, rapeseed, palmmeal and nut meals; and fats of animal origin such as egg yolk, lard, butter, poultry fat, tallow and fishoil.

The various processes disclosed herein can employ different types of high moisture materials depending upon the particular application. These high moisture materials can contain:

between about 50% and about 80% by weight water;
at least about 10% by weight carbohydrate; and
a member selected from the group consisting of:
  at least about 5% by weight protein,
  at least about 7% by weight amino acids, amino acid precursors, amino acid analogs, or a combination thereof,
  a combination of at least about 5% by weight protein and at least about 5% by weight amino acids, amino acid precursors, amino acid analogs, or a combination thereof,
  a combination of at least about 10% by weight protein, amino acids, amino acid precursors, and amino acid analogs, and
  at least about 10% by weight protein.

The ratio of carbohydrates to the various nitrogen-containing members in these high moisture materials can be in the range between about 1:1 and about 3:1.

When the high moisture material contains at least about 7% by weight amino acids, amino acid precursors, amino acid analogs, or a combination thereof, or a combination of at least about 10% by weight protein, amino acids, amino acid precursors, and amino acid analogs, the high moisture material can also contain a starch, a gum, or a combination thereof. The starch can be an unmodified starch or a combination of an unmodified starch and a modified starch. When the starch is an unmodified starch, it can be present in an amount of at least about 10% by weight. When the starch is a combination of an unmodified starch and a modified starch, the modified starch can be present in an amount of at least about 0.0% by weight. When a gum is employed, it can be present in an amount of from about 0.001% to about 5% by weight.

To enable hatchlings to more effectively utilize any fats which may be present in the high moisture material or to enable the hatchlings to more effectively utilize its yolk-based lipid and protein, the high moisture material may contain bile salts, cholesterol, surfactants, emulsifying agents, micelles, or an enzyme such as lipase, amylase, maltase, pepsin, trypsin, or other enzyme which commonly occur in the gastrointestinal system, or an enzyme such as keratinase which is not typically found in the gastrointestinal system but which has useful activities. The concentration of the digestion aid will depend upon the application but, in general, will be between about 0.01% and about 5% by weight of the dry matter.

The high moisture material may additionally contain vitamins and minerals. Vitamin additives may be selected, for example, from vitamin A, B12, biotin, choline, folacin, niacin, pantothenic acid, pyridoxine, riboflavin, thiamin, C, D, 25-hydroxy D, E, and K. Mineral additives may be selected, for example, from calcium, phosphorous, selenium, chlorine, magnesium, potassium, sodium, copper, iodine, iron, manganese and chromium pincolinate. The concentration of the vitamins and minerals will depend upon the application but, in general, will be between about 0.01% and about 5% by weight of the dry matter.

Bacterial, yeast or mold preparations, commonly referred to as probiotics or direct fed microbials, have been administered orally or added to animal feeds to provide various benefits such as altering the gastrointestinal microflora/microbiota of poultry and other animals. Those microbial additives which have been approved for use are identified in the annual Feed Additive Compendium published by The Miller Publishing Company (Minnetonka, Minn.) in cooperation with The Animal Health Institute and the Direct-fed Microbial, Enzyme and Forage Additive Compendium published by The Miller Publishing Company. Among the direct-fed microbials which have been approved are strains of the lactic acid bacteria, particularly those classified in the following genera: Lactobacillus, Lactococcus, and Enterococcus. Included among these are the following species: *Lactobacillus reuteri, Lactobacillus acidophilus, Lactobacillus bulgaricus, Lactobacillus plantarum, Lactobacillus casei, Lactobacillus lactis, Lactococcus lactis, Lactococcus thermophilus, Lactococcus diacetylactis*, and *Enterococcus faecium*. In addition to these lactic acid bacteria, some species of Bacillus (such as *Bacillus subtilis* and *Bacillus toyoi*), some species of Streptococcus (such as *Streptococcus faecium*), and yeasts and molds (such as *Saccharomyces cerevisiae, Aspergillus oryzae*, and Torulopsis sp.) have also been used as direct fed microbials.

The high moisture material of the present invention, therefore, may be used as a vehicle to administer direct-fed microbials to poultry and other animals. When used for this purpose, the high moisture material should contain sufficient colony forming units of the yeast or bacterium to be of benefit to the animal. In general, the high moisture material used as a direct fed microbial should contain at least about $10^2$, preferably about $10^4$, and more preferably about $10^6$ colony forming units of bacteria or at least about 10, preferably about $10^2$, and more preferably about $10^4$ colony forming units of yeast per gram of composition. The yeast or bacterium may be incorporated into the high moisture material prior to solidification or it may be deposited on or in the high moisture material after it has solidified. Although the high moisture material may be fed at anytime to alter the gastrointestinal microflora/microbiota of or provide other benefits to the animal, it is preferably fed to poultry as soon as possible after hatching to establish the direct fed microorganism(s) as the dominant flora or culture in the gastrointestinal tract and thereby exclude potential pathogens.

The high moisture material may additionally be used as a vehicle to deliver a variety of other substances to poultry and other animals. For example, the high moisture material may contain a peptide such as epidermal growth factor, transforming growth factor, granulocyte-macrophage colony stimulating factor, erythropoietin, bombesin, fibroblast growth factor, keratinocyte growth factor, nerve growth factor, vascular endothelial growth factor, bovine or other somatotropin or insulin-like growth factor (IGF-I or IGF-II). The high moisture material may also contain a steroid or polypeptide hormone such as, estrogen, glucocorticoids, insulin, glucagon, gastrin, calcitonin or somatotropin. The high moisture material may further contain an antibiotic approved for use in animal feed such as bacitracin, BMD (bacitracin methylenedisalicylate), lincomycin, or virginiamycin or other therapeutic drug. The high moisture material may also additionally contain a natural or synthetic antioxidant such as ethoxyquin, tocopherol, BHT (butylated hydroxytoluene), BHA (butylated hydroxyanisole), vitamin C or glutathione; a receptor, transfer factor, chelator or complexing agent which modifies release rates of nutrients or other bioactive compounds; an immunoactive agent such as cytokines, vaccines and other immunomodulators, immunoglobulins, antigens, killed cells, attenuated strains, toxins, or adjuvants; or a palatability modifier or intake regulator such as food coloring, grit, oyster shell, whole seeds or grains. These substances can be used alone or in combination with one another. The concentration of these additives will depend upon the application but, in general, will be between about 0.0001% and about 10% by weight of the dry matter, more preferably between about 0.001% and about 7.5%, most preferably between about 0.01% and about 5%.

Food colorings useful in the present invention include, for example, red, green, blue, blue-green, black, and beige.

Substances useful as palatability modifiers or intake regulators in addition to those mentioned above include triglycerides; fish products such as fishmeal and fish oils; spices such as sage, thyme, cloves, etc.; clonidine; gums and hydrolyzed gums such as guar gum, xanthan gum, algin, etc.; gastrin antagonists; cholecystokinin antagonists; amino acids such as methionine, tyrosine, phenylalanine, etc.; naloxone; pancreatic polypeptide; norepinephrine; melatonin antagonists; thyroid hormones such as thyroxine, T3, T4, etc.; and pentobarbital.

Adjuvants that can be incorporated into the high moisture material can be of several different types, e.g., microbiologically-derived substances, viruses, lectins, polysaccharides, oils, peptides, polypeptides, and proteins, and various nucleic acids. Microbiologically-derived substances include materials produced by, or which are cellular components of, microorganisms such as bacteria, fungi such as yeasts, etc. Prior to the present investigations, it was not known that such substances could be used as orally effective adjuvants in poultry to stimulate the immune system and/or to enhance the resistance of poultry to pathogens or other stresses, including exposure to heat or cold, dehydration, ammonia fumes in litter, transport, etc. Similarly, it was not previously known that such adjuvants, when orally administered, could positively affect the health, livability, weight gain, or feed conversion efficiency of poultry.

Microbiologically-derived adjuvants comprise a variety of different types of substances. For example, these can include lysates of bacteria such as Haemophilus sp., Diplococcus sp., Neisseria sp., etc.; trehalose 6,6-diesters (cord factor) and synthetic analogues thereof; muramyl dipeptide (N-acetyl-muramyl-L-alanyl-D-isoglutamine) and synthetic analogues thereof; L-seryl and L-valyl derivatives of muramyl dipeptide; killed bacteria and derivatives thereof such as Escherichia spp, Clostridia spp, Salmonella spp, Lactobacillus spp, Streptococcus spp, Bacillus Calmette-Guerin, Mycobacterium spp, Bordetella spp, Klebsiella spp, Brucella spp, Propionibacterium spp such as *Corynebacterium parvum*, Pasteurella spp, Norcardia spp such as *Norcardia rubra* and derivatives thereof such as Norcardia water soluble mitogen; Staphylococcus cell wall products; bestatin; killed yeast such as Saccharomyces spp and Candida spp; yeast derivatives such as zymosan, glucan, and lentanin; endotoxins and enterotoxins such as Cholera toxin; cell wall peptido-glycans; and bacterial ribonucleoproteins. Microbio-logically-derived adjuvants also include viruses, for example Avipoxviruses and Parapoxviruses.

Useful lectins include, for example, concanavalin A, pokeweed mitogen, and phytohemagglutinin.

Useful polysaccharides include mannans such as acemannan, $\beta$-(1,4)-linked acetylated mannan, and mannan oligosaccharide; glucans; carrageenan and iota carrageenan; hemicelluloses; levans; agar; tapioca; dextrins; dextrans, for example dextran sulfate salts of various molecular weights; and lipopolysaccharides.

Oil emulsions useful as adjuvants can be produced using mineral oil, peanut oil, and sesame oil, for example.

Useful peptides and macromolecules include cytokines such as lymphokines, interleukins, Transfer Factor, Macrophage Activating Factor, Migration Inhibitory Factor, and mitogenic factors for lymphocytes; nucleic acid digests; interferon and interferon inducers such as BRL 5907; double stranded complementary RNA homopolymers such as poly I:C and poly A:U; immune RNA; thymic hormones such as thymostimulin, thymulin, thymosin, and thymopoietin; protease inhibitors; chemotactic factors for macrophages and other cells; tuftsin; and serum albumin (bovine, human, acetylated derivatives, beads, etc.).

Finally, a variety of other substances that can be employed as adjuvants in the present invention include saponins such as QuilA and Iscoms; tiabenedezole; tylorone; statolon; maleic anhydride-divinyl ether; pyran copolymers; amphotericin B; liposomes; silica; calcium phosphate; glycerol; betaine; protodyne; cyanidanol; imuthiol; picibanil; isoprinosine; lentinan; azimexon; lecithin; levamisole; vitamin A and other retinols; vitamin E and other tocopherols; antioxidants, such as ethoxyquin; aluminum salts, such as sulfates and phosphates, including alum (KAl$(SO_4)_2 \cdot 12H_2O$); aluminum hydroxide; and aluminum oxide.

Vaccines useful in the present invention include those effective against common diseases in poultry such as Newcastle's Disease, Marek's Disease, infectious bursal disease, infectious bronchitis, enteritis, coccidiosis, etc. These vaccines include Newcastle's vaccine, Marek's Disease vaccine, infectious bursal disease vaccine, infectious bronchitis vaccine, and CocciVac®, for example. When used in conjunction with the high moisture material of the present invention, these vaccines can be administered to young birds within 0 to about 10 days of hatching orally, via yolk sac injection, subcutaneously, in ovo, or via inhalation by mist or spray.

A formulation satisfying the nutrient specifications of the high moisture material of the present invention may be prepared, for example, from the following ingredient mix (based upon the weight of the non-aqueous fraction of the high moisture material):

| | |
|---|---|
| soybean meal | 58% |
| dried egg white | 8% |
| corn starch | 4% |
| corn meal | 30% |
| Alimet ® | 0.5% |
| propionic acid | 0.5% |
| citric acid | to pH 3.5–4 |

High moisture materials containing these ingredients (and optionally one or more of the other additives described herein) can be made by dry mixing the ingredients, adding hot water (80° C.) and quickly mixing the wetted ingredients while maintaining the temperature above the starch gelation temperature for at least one minute. The mixture is then stirred and pressed into a dish, cylinder, mold, or other vessel or container.

Although a high moisture material may be prepared from a poultry starter diet formulation, such simple mixtures readily allow the escape of free water which is potentially deleterious. Not only could the hatchling chicks suffer from evaporative cooling as a result of being wetted by the released moisture, they could suffer from consuming high moisture material which contains insufficient moisture. In addition, a loss of moisture could cause a substantial change in the texture of the high moisture material, changing it from a material which the hatchling chicks can break apart by pecking and consume to one which is hard or "leathery" and inaccessible to the birds. It is preferred, therefore, that the high moisture material have an initial moisture content of at least about 40% by weight water and that the high moisture material retain substantially all of its water under the conditions at which it is being provided to the chicks. More preferably, the high moisture material will retain at least 80% and most preferably at least about 90% of its water content when exposed to a temperature of 80° C. and a relative humidity of 70% for 24 hours. To improve the water-retention capability of the high moisture material, humectants, gums, proteins or other ingredients may be included in the formulation.

Similarly, the digestibility of ingredients could be improved with additions to the formulation such as, but not limited to, enzymes, bile salts or surfactants. Similarly, overall performance may be improved with the addition of selected micro ingredients, minerals, microorganisms, growth promotants, hormones, prostaglandins such as $E_2$ or other factors which promote enhanced digestive enzyme activity, nutrient absorption or maturation of the gastrointestinal system as a whole.

In general, highly available protein sources might include hydrolyzed poultry protein, hydrolyzed casein, or peptone. In contrast, less available protein sources such as by-product meals or vegetable proteins might be fed in combination with factors such as proteases or microorganisms that secrete proteases to increase digestibility. Similarly, carbohydrates such as glucose may be chosen for high availability, or more complex sources such as ground corn or potato starch may be supplemented with enzymes or subjected to gelation to increase their availability. Digestibility of saturated fats could be improved through the addition of lipase, bile salts or surfactants. Thus, the formulation would include either highly available ingredients or additives or handling methods which improve digestion of less available ingredients in very young birds. The ingredients would be administered in a semi-solid or solid form.

In addition, it has been demonstrated that the gastrointestinal system of young birds is not able to use certain ingredients such as tallow with the same efficiency as mature birds (Fredde et al., *Factors Affecting the Absorbability of Certain Dietary Fats in the Chick*, J. Nutrition, Vol. 70, pp. 447–452 (1960); Gomez et al., *The Use of Bile Salts to Improve Absorption of Tallow in Chicks, One to Three Weeks of Age*, Poultry Science Vol. 55, pp. 2189–2195 (1976); Polin et al., *The Effect of Bile Acids and Lipase on Absorption of Tallow in Young Chicks*, Poultry Science, Vol. 59, pp. 2738–2743 (1980); Sell et al., *Influence of Age on Utilization of Supplemental Fats by Young Turkeys*, Poultry Science, Vol. 65, pp. 546–554 (1986)). Ontogenetic changes which accompany improved digestion include increased levels of pancreatic and intestinal enzymes (Krogdahl et al., *Influence of Age on Lipase, Amylase, and Protease Activities in Pancreatic Tissue and Intestinal Contents of Young Turkeys*, Poultry Science, Vol. 68, pp. 1561–1568 (1989); Sell et al., *Intestinal Disaccharidases of Young Turkeys: Temporal Development and Influence of Diet Composition*, Poultry Science, Vol. 68, pp. 265–277 (1989); Noy et al., *Digestion and Absorption in the Young Chick*, Poultry Science, Vol. 74, pp. 366–373 (1995)), overall gut surface area for absorption (Nitsan et al., *Growth and Development of the Digestive Organs and Some Enzymes in Broiler Chicks After Hatching*, British Poultry Science, Vol. 32, pp. 515–523 (1991); Nitsan et al., *Organ Growth and Digestive Enzyme Levels to Fifteen Days of Age in Lines of Chickens Differing in Body Weight*, Poultry Science, Vol. 70, pp. 2040–2048 (1991); Sell et al., *Developmental Patterns of Selected Characteristics of the Gastrointestinal Tract of Young Turkeys*, Poultry Science, Vol. 70, pp. 1200–1205 (1991)), and changes in nutrient transporters (Shehata et al., *Development of Brush-Border Membrane Hexose Transport System in Chick Jejunum*, Am. J. Physiol, Vol. 240, pp. G102–G108 (1981); Buddington et al., *Ontogenetic Development of Intestinal Nutrient Transporters*, Annu. Rev. Physiol., Vol. 51, pp. 601–619 (1989); Moreto et al., *Transport of L-Proline and α-Methyl-D-Glucoside by Chicken Proximal Cecum During Development*, Am. J. Physiol, Vol. 260, pp. G457–G463 (1991)). The high moisture material of the present invention would minimize or exclude poorly used ingredients and substitute more highly available ingredients as assessed by subsequent bird performance.

The quantity of the high moisture material fed will be a function of the animal species, age, environmental conditions such as temperature and humidity and, in the case of poultry, the length of the preplacement period, i.e, the total time consumed in the post-hatch holding period, the processing period and in transit to the poultry production farm. In general, however, at least about 5 grams of high moisture material per chick per day should be provided to 0 to 2 day old chicks, about 10 grams of high moisture material per chick per day should be provided to 2 to 3 day old chicks, and up to about 20 grams of high moisture material per chick per day should be provided to 4 to 7 day old chicks.

As previously noted, chicks conventionally are placed with poultry production farms within about 2 days of hatching. This practice has developed, in part, out of the fact that hatchers typically do not provide food or water to the hatchlings and the fact that the hatchlings must receive water and a source of nutrition by about 3 days or else they suffer.

Because the composition of the high moisture materials of the present invention can be controlled to meet the changing nutritional requirements of the hatchlings as they mature, it may become practical for hatchers to delay sending chicks to poultry production farms for a longer period of time or to ship chicks a greater distance without experiencing many of the difficulties associated with providing water and nutrition to the chicks. Thus, for example, hatchers could conveniently feed the high moisture material of the present invention to the chicks for a period of about 3 to about 7 days from hatching before shipping them on to the poultry production farms. Alternatively, the chicks could be shipped from the hatcher to an intermediate facility where they could be fed the high moisture material for a period of about 7 days and then shipped to the standard poultry production farm. Either approach would allow the poultry production farms to more efficiently utilize their houses without burdening the hatchers with feeding the hatchlings water and dry food.

The following examples will illustrate the invention.

EXAMPLE 1

The performance of 1 to 4 day old birds, i.e., birds which were no less than 1 day old and no more than 4 days old at the start of the test as measured from hatching for each bird, fed high moisture solids consisting of agar (1.5% agar and 98.5% by weight water) or agar and egg yolk (1.5% agar, 10% egg yolk and 88.5% by weight water) were compared to fasted and water deprived birds. The results are presented in Table 1. Birds initially lost weight on all feeding regimes and agar alone gave no benefit in either cumulative gain or cumulative feed-to-gain ratio ("FTG"). Agar plus yolk showed an effect on cumulative gain on days 6 and 13, but cumulative feed-to-gain ratio (sometimes referred to herein as cumulative feed efficiency) was poorer than for fasted birds. The data also suggest that hydration alone (agar treatment) with or without yolk conferred no cumulative feed efficiency benefit in this study. Cumulative livability was improved by feeding either water-containing formulation.

25% dry matter high moisture solid again was superior to the others whether fed for 24 or 48 hr. Cumulative feed intake subsequent to the 48 hr treatment period was higher when birds were given high moisture solids than when they were fasted. This was the case for formulations containing 25, 50 or 100% dry matter. Cumulative livability data suggest that the high moisture solids containing a greater percentage of dry matter are associated with lower livability than the fasted control or 25% dry matter formulations.

TABLE 2

Growth of Birds Fed Starter Feed and Moisture Combinations

| Treatment | Cumul. Gain Day 13 | Cumul. FTG Day 13 | BW Cumul. FTG Day 13 | Cumul. intake Day 13 | Cumulative Livability Day 13 |
| --- | --- | --- | --- | --- | --- |
| Fasted 24 h | 280.9 g | 1.316 | 1.292 | 369.8 g | 100% |
| Formulation 24 h Dry Matter 25% | 303.5 g | 1.319 | 1.285 | 400.3 g | 100% |
| Formation 24 h Dry Matter 50% | 269.0 g | 1.342 | 1.323 | 360.8 g | 100% |
| Formation 24 h Dry Matter 100% | 286.7 g | 1.312 | 1.285 | 375.8 g | 94% |
| Fasted 48 h | 222.8 g | 1.371 | 1.372 | 304.6 g | 96% |
| Formation 48 h Dry Matter 25% | 284.6 g | 1.274 | 1.248 | 362.5 g | 100% |
| Formation 48 h Dry Matter 50% | 267.0 g | 1.353 | 1.335 | 360.4 g | 83% |
| Formation 48 h Dry Matter 100% | 237.9 g | 1.394 | 1.389 | 328.4 g | 83% |

EXAMPLE 3

In this example, groups of one to four day old birds were given 20 g each of a high moisture solid consisting of gelatin and Alimet® (2-hydroxy-4-(methylthio)butanoic acid) base

TABLE 1

Growth of Birds Fed Nothing or Formulations Consisting of Agar (1.5%) with and without Egg Yolk (10%)

| Trt | Cumul. Gain Day 3 | Cumul. Gain Day 6 | Cumul. FTG Day 6 | Cumul. Gain Day 13 | Cumul. FTG Day 13 | Cumulative Feed Intake Day 13 | Cumulative Livability Day 13 |
| --- | --- | --- | --- | --- | --- | --- | --- |
| Fasted 24 h | −8.0 | 35.8 g | 1.66 | 1.95.5 g | 1.40 | 274 g | 94% |
| Agar | −7.2 | 32.8 g | 1.95 | 193.7 g | 1.41 | 273 g | 100% |
| Agar & Yolk | −7.8 | 37.5 g | 1.70 | 197.4 g | 1.43 | 282 g | 100% |

EXAMPLE 2

In this example, groups of one to four day old birds were fed for 24 or 48 hours a high moisture solid consisting of starter feed and water. Pens were given enough high moisture solid for each bird to consume 10 g. The feed was present at either 25, 50 or 100% of the high moisture solid. From Table 2 it appears that the high moisture solid containing 25% dry matter gave the best cumulative gain after feeding either 24 or 48 hr. It should be noted, however, that all high moisture solids showed cumulative gain superior to the fasted controls. When cumulative feed efficiency, was corrected for differences in body weight (BW FTG), the with additions of either corn starch or corn starch and lysine. The dry matter content of the high moisture solid was about 5% and the amount of each of the dry matter constituents, based upon the weight of the high moisture solid for each formulation, was as indicated in Table 3. The formulation containing corn starch, gelatin and Alimet® showed cumulative gain and livability superior to the fasted control and the other two formulations. Treatments 2 and 3 also showed superior cumulative feed intake when compared with the fasted control, but the formulations tended to liquify at the brooding temperature and could cause problems in brooding and transit boxes.

TABLE 3

Growth of Birds Fed Formulations Containing Starch, Gelatin, Alimet and Lysine Combinations

| Trt | Corn Starch | Gelatin | Alimet ® | Lysine | Cumul Gain Day 14 | Cumul FTG Day 14 | Cumul Intake Day 14 | Cumulative Livability Day 14 |
|---|---|---|---|---|---|---|---|---|
| Fasted 24 hr | | | | | 297.8 g | 1.22 | 358 g | 95% |
| 1 | 0g | 2.5% | .13% | 0 | 290.8 g | 1.32 | 340 g | 80% |
| 2 | 2.5% | 2.5% | .13% | 0 | 317.7 g | 1.23 | 392 g | 100% |
| 3 | 2.5% | 2.5% | .13% | .13% | 289.1 g | 1.34 | 360 g | 80% |

EXAMPLE 4

Groups of one to four day old birds were fed formulations containing sources of fats and protein administered with and without added lipase to assist in the digestion of the fat. All formulations contained corn starch, Alimet, lysine and the bile salt, chenodeoxycholic acid. In one case, protein and fat were provided together in the form of yolk solids. In the second case, poultry protein and soy oil were used to provide the protein and fat. The dry matter content of the high moisture solid was about 25% and the amount of each of the dry matter constituents, based upon the weight of the high moisture solid for each formulation, was as indicated in Table 4. Table 4 indicates that the improved cumulative gains and cumulative feed efficiencies were observed in all formulation treatments. Lipase did not appear to be enhance the availability of these complex fat sources. Superior early cumulative feed intake was achieved with yolk solids in the absence of additional lipase. It should be noted that yolk was also used in Example 1, but bird response was not evident in the absence of a source of carbohydrates, bile salts, a methionine source and added lysine.

TABLE 4

Growth of Birds Fed Formulations Containing Sources of Protein and Fat, with and without Lipase (Corn starch: 2.5%, Alimet: .05%, Lysine .05%, Chenodeoxycholic acid: .02%)

| Trt | Addition | Fat | Protein | Cumul. Gain Day 12 | FTG Day 12 | Cumul. intake Day 12 | Cumulative Livability Day 12 |
|---|---|---|---|---|---|---|---|
| Fasted | | | | 253.6 g | 1.30 | 329.2 g | 100% |
| 1 | Egg Yolk (11%) | 7.7% | 3.3% | 284.4 g | 1.22 | 345.6 g | 100% |
| 2 | Lipase (2%) Egg Yolk (11%) | 7.7% | 3.3% | 254.0 g | 1.24 | 312.2 g | 100% |
| 3 | Soy Oil (10%) Poultry Protein (10%) | 10% | 7.5% | 264.3 g | 1.25 | 331.2 g | 95% |
| 4 | Lipase (2%) Soy Oil (10%) Poultry Protein (10%) | 10% | 7.5% | 257.9 g | 1.26 | 312.4 g | 100% |

EXAMPLE 5

Groups of one to four day old birds fed agar (1.5% agar and 98.5% water) and agar plus a direct fed microbial (1.5% agar, 88.5% water, 10% Biomate direct fed microbial including the microbial carrier) were compared to a fasted control. The direct fed microbial ("DFM") consisted of two species of Lactobacilli and two species of Bacilli. The direct fed microbial contained $2.2 \times 10^8$ colony forming units per gram of material for each of the Lactobacilli species and $5.5 \times 10^8$ colony forming units per gram of material for each of the Bacilli species with each pen of 8 birds receiving 1 gram of product. Although the cumulative feed efficiency of this treatment was poorer than that of agar alone, cumulative gain appeared to increase in the presence of water and the DFM. The DFM, therefore, provided some benefit on its own and to optimize this effect more nutrients should be added to the high moisture solid.

TABLE 5

Growth of Birds Fed Agar (1.5%) and Agar Containing a Direct Fed Microbial Consisting of *Lactobacillus acidophilus* and *lactis*, and *Bacillus subtilis* and *licheniformis* (10%)

| Treatment | Cumulative Gain Day 21 | Cumulative Feed to Gain Day 21 | Cumulative Feed Intake Day 21 | Cumulative Livability Day 21 |
|---|---|---|---|---|
| Fasted 24 h | 710.3 g | 1.388 | 985.8 g | 98% |
| Agar (1.5%) | 720.5 g | 1.386 | 998.0 g | 98% |
| Agar (1.5%) DFM (10%) | 724.2 g | 1.387 | 1004.4 g | 98% |

EXAMPLE 6

This example shows the response of one to four day old hatchlings to casein, enzyme hydrolyzed casein and casein administered with a source of proteolytic activity. The high moisture solid contained 85% water with a balance of constituents as indicated in Table 6. In treatment 3, 0.6% pepsin (based upon the weight of the high moisture solid) was added to the formulation and in treatment 4, a microbe which secretes a proteolytic enzyme was added. All formulation treatments showed superior cumulative gain, cumulative feed efficiency and livability when compared to the fasted control.

TABLE 6

Growth of Birds Fed Formulations with Casein, Hydrolyzed Casein, Casein with Pepsin or Casein with *B. licheniformis* ($2 \times 10^6$/bird) (Ground corn: 10%, Agar: .25%, Alimet: .125%, Lysine: .04)

| Trt | Casein | Cumulative Gain Day 12 | Cumulative Feed to Gain Day 12 | Cumulative Feed Intake Day 12 | Cumulative Livability Day 12 |
|---|---|---|---|---|---|
| Fasted 24 h | | 207.2 g | 1.34 | 303.4 g | 79% |
| 1 | Casein (10%) | 249.3 g | 1.21 | 301.7 g | 92% |
| 2 | Hydrolyzed Casein (10%) | 234.8 g | 1.19 | 280.1 g | 96% |
| 3 | Casein (10%) Pepsin (.6%) | 234.8 g | 1.26 | 293.7 g | 91% |
| 4 | Casein (10%) *B. licheniformis* | 248.8 g | 1.19 | 296.0 g | 91% |

EXAMPLE 7

In this example, zero to two day old birds were fed formulations consisting of 10% dry matter in the form of corn starch (2.5%), protein (5%), and glucose (2.5%), based upon the weight of the high moisture solid. Birds were treated for 24, 48 or 72 hours, to test the possibility of treating birds over the total preplacement period of approximately 2 days in the hatching incubator and 1 day in transit. All formulation treated birds showed cumulative gain superior to birds fasted for an equivalent period. In addition, the birds treated with formulation for 24 and 48 hours also showed superior cumulative feed efficiencies. The response appeared to decline at the 72 hour time point. It appears from these data that 10% dry matter is sufficient to improve performance of young birds over a 2 day period, but that a higher concentration of nutrients may be required by the third day. It should be noted that for each time period, livability of formulation fed birds was superior to fasted controls.

TABLE 7

Growth of Birds Fed Hatchery Formulations Consisting of Corn Starch (2.5%), Porcine Plasma (5%), Agar (.5%), Alimet (.125%), Lysine (.125%), Glucose 2.5%; Total 10% Dry Matter)

| Treatment | Cumulative Gain Day 16 | Cumulative Feed to Gain Day 16 | Cumulative Feed Intake Day 16 | Cumulative Livability Day 16 |
|---|---|---|---|---|
| Fasted 24 h | 405.4 g | 1.431 | 580.1 g | 93% |
| Formulation 24 h | 435.6 g | 1.422 | 619.4 g | 96% |
| Fasted 48 h | 369.3 g | 1.425 | 526.3 g | 95% |
| Formulation 48 h | 391.7 g | 1.413 | 553.5 g | 100% |
| Fasted 72 h | 331.1 g | 1.430 | 473.5 g | 91% |
| Formulation 72 h | 348.6 g | 1.456 | 507.6 g | 93% |

EXAMPLE 8

In this example, the growth of chicks fed nothing, formulations solidified with dehydrated egg white, whole egg or guar/xanthan gums, or a simple gruel of rice and corn was compared. Table 8 shows early bird performance as influenced by formulations solidified in various ways.

Treatment 1 was the fasted control. The formulation in treatments 2 and 3 consisted of corn meal (15%), corn starch (2%), soybean meal (12%) and either dehydrated egg white (3.6%) or whole egg (20%). Treatment 4 had slightly more soybean meal (16%) to compensate for the loss of the egg protein and was solidified with a combination of guar (0.35%) and xanthan (0.05%) gums. Treatment 5 was a simple gruel of rice (22.5%) and corn (22.5%). All formulations contained fumaric (1%) and propionic (0.5%) and a vitamin (0.1%) and mineral (0.05%) premix.

One to four day old birds were weighed (Table 8, body weight day 0) and treated with 10 gm/bird of a high moisture solid or fasted for 24 hours. The birds receiving high moisture solid received one of four high moisture solids designated in Table 8. Birds were then weighed again (body weight day 1) and all were offered water and starter feed for ad libitum consumption. As can be seen in Table 8, fasted birds initially lost weight while formulation treated birds either maintained or even gained weight. Day 6 performance, however, indicated that the higher protein formulations (2–4) were more beneficial than the simple rice and corn mixture. Both body weights and feed efficiencies of birds in treatments 2–4 were superior to those of treatment 5. All birds showed an improvement in early livability compared to fasted controls.

TABLE 8

Growth of Birds Fed Nothing or Formulations Solidified with Dehydrated Egg White, Whole Egg or Guar/Xanthan Gums, in Comparison to a Simple Gruel of Rice and Corn

| Trt | Treatment Description | Body Weight Day 0 | Body Weight Day 1 | Body Weight Day 6 | Feed to Gain Day 6 | Livability Day 6 |
|---|---|---|---|---|---|---|
| 1 | Fasted Control | 43.5 | 41.8 | 140.9 | 1.305 | 69% |
| 2 | Dehydrated Egg White | 43.4 | 44.8 | 154.9 | 1.121 | 98% |
| 3 | Whole Egg | 43.6 | 45.8 | 156.1 | 1.175 | 98% |
| 4 | Guar and Xanthan Gum | 43.1 | 43.4 | 155.6 | 1.167 | 98% |
| 5 | Rice and Ground Corn | 43.9 | 45.1 | 147.6 | 1.200 | 100% |

EXAMPLE 9

In this example, the water retention characteristics of the various formulations described in Example 8 was compared to that in a simple ground corn and rice gruel. After 24 hours, formulations in which egg or gums were added to bind the water held more moisture than did the simple hot water slurry of rice and ground corn. When these were fed to one to four day old chicks, birds eating the rice and ground corn gruel were noted to be damp, although no measurable water escaped from any of the mixtures. The results are presented in Table 9.

TABLE 9

Water Retention (%) in Formulations after 24 hours at 80, 90 or 100 C. and 40% Humidity

| | Water Remaining in Formulation After 24 Hours | | | | | |
|---|---|---|---|---|---|---|
| | 80 C. | | 90 C. | | 100 C. | |
| Formulation | % | g/kg | % | g/kg | % | g/kg |
| Dehydrated Egg White | 26.5 | 175 | 15.5 | 102 | 16.5 | 109 |
| Whole Egg | 26.0 | 172 | 22.5 | 149 | 15.5 | 102 |
| Guar Xanthan Gum | 24.0 | 166 | 22.5 | 156 | 17.0 | 118 |
| Rice and Ground Corn | 14.5 | 80 | 2.8 | 15 | 0 | 0 |

EXAMPLE 9a

Table 9a shows water loss by high moisture solids kept at 80° C. and 70% humidity. Formulations 1–4 contained guar and xanthan gums (0.6–1%), 20–22% soybean meal and about 16% corn meal, with the balance as water. Humectant levels ranged from 1 g (modified corn starch) to 50 g (propylene glycol and glycerol). Formulations 5 and 6 were included as examples of simple formulations which did not include a humectant. Formulation 5 consisted of 21% soybean meal, 11% oats and 8.5% rice, with the balance as water. Prior to the experiment shown in Table 9a, all formulations were kept at room temperature overnight to allow the mixtures to absorb the water. In the absence of a humectant, a gum based gel lost 19% of its water in 24 hours and 34% after 48 hours. High moisture solids containing the humectants propylene glycol and glycerol lost 0–10% of their water in 24 hours and 4–17% after 48 hours. The modified corn starch did not perform as well under these conditions as did the other humectants. Simple mixtures of grain and rice retained the least water under these conditions, losing 24% water over the first 24 hours and 47–53% of their water by 48 hours.

TABLE 9a

Water Retention (80 C., 70% Humidity) at 24 and 48 hour by High Moisture Solids Containing Gums or Humectants in Comparison to Simple Mixtures of Gains, Soybean Meal and Rice

| Trt | Formulation Contents | Other | Loss at 24 h (%) | Loss at 48 h (%) |
|---|---|---|---|---|
| 1 | Soybean Meal, Corn Meal & Gum | | 19% | 33% |
| 2 | Soybean Meal, Corn Meal & Gum | Modified Corn Starch | 20% | 42% |
| 3 | Soybean Meal, Corn Meal & Gum | Propylene Glycol | 0% | 4% |
| 4 | Soybean Meal, Corn Meal & Gum | Glycerol | 10% | 17% |
| 5 | Soybean Meal, Rice & Oats | None | 24% | 47% |
| 6 | Ground Corn & Rice | None | 24% | 53% |

EXAMPLE 10

In this example, samples from formulations containing soybean meal (12%), corn meal (17%) and either whole egg (20%) or guar/xanthan gum (4%) stabilized with fumaric (1%) and propionic (0.5%) acids were compared to a simple corn (23%) and rice (23%) mixture for microbial growth. All mixtures were stored sealed (except for sampling) at room temperature. Plates were incubated for 3 days at 37° C. in a saturated atmosphere. MacConkey agar was included to evaluate the growth of Gram negative organisms such as *E. Coli*. From Table 10 it is clear that the rice and corn mixture was not stable and supported high levels of microbial growth when stored at room temperature in a sealed bag. The heating procedure does not destroy bacillus spores, and these would be the source of the colonies seen in the blood agar at day 1 and 2 in the formulation containing guar and xanthan gums. It is clear, however, that bacilli were not multiplying in the formulation itself, because numbers did not increase with time. The organisms present in the rice and corn gruel included Gram negative rods, Gram positive cocci and yeast.

The formulation made with soybean meal (11%), corn meal (15%), corn starch (2%), dehydrated egg white (6%) and stabilized with citric (1%) and propionic (0.5%) acids was also tested for stability to microbial growth. Samples were stored for 9 weeks without showing any indication of microbial growth when tested on blood agar and MacConkey agar. There was no mold growth evident on the samples and no indication of separation of water from the high moisture solid over this period of time.

TABLE 10

Microbial Growth of a 1:1000 Dilution of Formulation

Number of Colonies in 0.1 ml of a 1:1000 Dilution

| | Whole Egg | | Guar & Xanthan Gums | | Rice & Corn Gruel | |
|---|---|---|---|---|---|---|
| Day | Blood Agar | MacConkey | Blood Agar | MacConkey | Blood Agar | MacConkey |
| Day 1 | 0 | 0 | 1 | 0 | 4 | 0 |
| Day 3 | 0 | 0 | 2 | 0 | 1067 | 53 |
| Day 5 | 0 | 0 | 0 | 0 | 1000 | 0 |
| Day 9 | 0 | 0 | 0 | 0 | 1100 | 90 |

EXAMPLE 11

This example shows the proximate analysis of several high moisture solids in comparison to mixtures of rice and various grains with as much water as the combination will hold (excess water poured off). Values for carbohydrates are obtained by difference. Performance studies using live birds have indicated that the optimum protein level in a high moisture solid fed to day old birds is 10–11%. Using dry matter levels of 33%, feeding a level of 10% protein and 20% carbohydrate in a high moisture solid resulted better day 6 gain and feed conversion results (Example 8) than did a rice and corn mixture containing 4% protein and 35% carbohydrate. A protein level of 10% is not possible using a mixture based on a whole grain and rice or whole grain alone, even with 100% dry matter. Even if the grain were relatively high in protein, such as wheat (maximum 15%), protein levels higher than 7–8% would not be possible in a mixture containing 50% water. With a mixture of wheat and water, a protein level of 10.5% would require 70% dry matter. The results are presented in Table 11.

TABLE 11

Proximate Analysis of Formulations of Corn and Soybean Meal and Containing Dehydrated Egg White to Bind the Water in Comparison to Various Rice, Corn and Water Mixtures

| | Proximate Analysis | | | | |
|---|---|---|---|---|---|
| Formulation | Carbohydrate % | Protein % | Fat % | Ash % | Water % |
| Soy Meal, Corn Meal & Dehydrated Egg White | 19.1 | 10.3 | .7 | 1.0 | 68.4 |
| Soy Meal, Corn Meal & Whole Egg | 20.0 | 9.4 | 2.2 | 1.0 | 66.8 |
| Soy Meal, Corn Meal & Guar/Xanthan Gum | 23.7 | 10.7 | .2 | 1.2 | 63.4 |
| Rice | 33.8 | 3.1 | .8 | .2 | 62.1 |
| Corn | 41.9 | 4.5 | 2.1 | .6 | 50.2 |
| Rice and Corn | 34.6 | 3.9 | 1.3 | .4 | 41.0 |
| Rice and Oats | 25.5 | 4.3 | 1.2 | .5 | 68.5 |
| Oats, Rice, Rye, Wheat, Triticale and Buckwheat | 15.4 | 3.7 | 1.1 | .5 | 74.8 |

EXAMPLE 12

The objective of this experiment was to determine the optimum ratio of fat, protein, and carbohydrate in a formulation with a 25% solids composition. An experimental design was generated to meet the stated objective and it was implemented as a 96 pen, 41 day study. In this study, 1–4 day old chicks were fed the formulation or were fasted for 48 hours. The results are present in FIG. 1. The performance parameter illustrated in FIG. 1 is the estimated feed conversion for a 2 kg broiler at 41 days. A response surface model was made for feed conversion corrected to a constant live weight. It was found that fat had a large negative impact on performance. The birds treated with greater than 5% fat showed losses in live weight and increased feed conversion. The best performance for this 25% dry matter formulation occurred with the protein and carbohydrate treatments where the birds exhibited body weight corrected feed conversions of 1.72–1.73. Mortality was lowest at 21 days for treatments with higher levels of protein, and highest with treatments that contained significant amounts of fat. Data from this experiment indicate that the optimum digestible carbohydrate level is above 8%.

EXAMPLE 13

Figure 2:
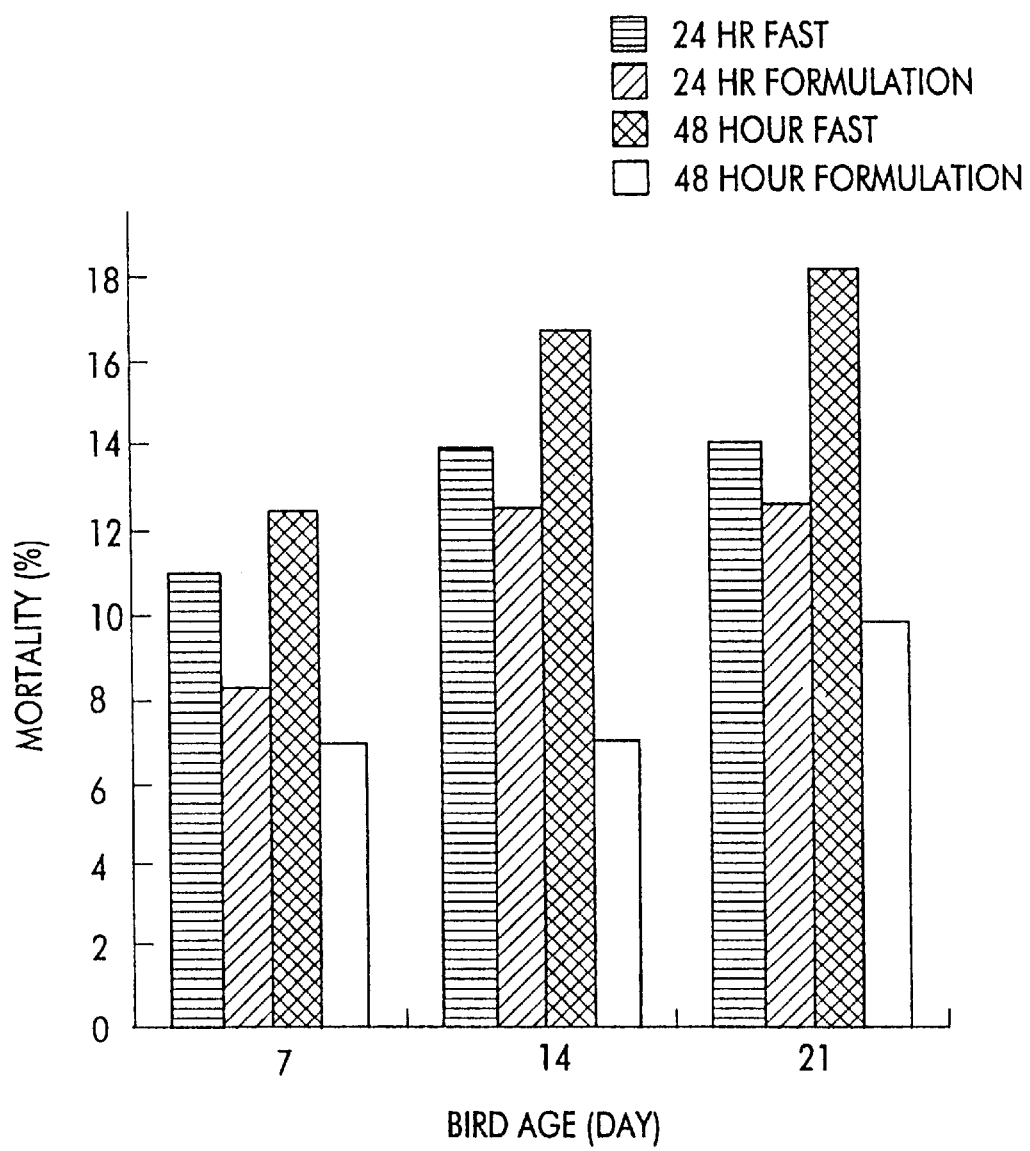
FIG. 2 is a bar graph depicting the results of Example 13.

Early mortality in turkey poults is a particular problem in this industry. It is ascribed to a number of factors, including failure of the birds to ingest feed and water ad libitum due to an excessively long time between hatch and placement. In this experiment, groups of one to four day old turkey poults were fed a 33% dry matter formulation containing less than 1% fat, 9–10% protein, and 22–23% carbohydrates, or were fasted and deprived of water for either 24 or 48 hours. On a percent dry matter basis, the formulation contained 44% corn meal, 6% corn starch, 36% soybean meal, 11% dehydrated egg white, 2% fumaric acid, and 1.5% propionic acid. As a percentage of the total formula-tion, this equated to 15% corn meal, 2% corn starch, 12% soybean meal, 3.6% dehydrated egg white, 0.7% fumaric acid, and 0.5% propionic acid. Afterwards, the birds were given a conventional feed formulation. As shown in FIG. 2, the performance of birds on this regime showed differences in 7, 14, and 21 day cumulative mortalities: birds fasted for 24 hours showed mortalities greater than those given formulation for 24 hours. This was further accentuated when birds were fasted or given formulation for 48 hours. In the group fasted for 48 hours, early mortality reached almost 20% by day 21, whereas birds given formulation over the same time period showed the least cumulative 21 day mortality in the study, i.e., less than 10%.

EXAMPLE 14

This experiment was performed to test the effect of feeding high moisture material of the present invention to newborn hatchlings before they are offered dry food ad libitum containing approximately 77% water, 1% fat, 11% carbohydrate, and 11% protein, on resistance of chickens to a disease challenge with or without previous vaccination to the pathogen. (The same basic composition was also used in the examples which follow). The term "disease challenge" refers to contact of poultry with a pathogen, causing a negative effect on a performance parameter such as health, livability, weight gain, or feed conversion efficiency. Treatments 1–4 received no feed or water, while the high moisture material (designated "1027" in FIG. 3) was the sole source of nutrition and hydration for the first two days of the experiment for treatments 5–8. An oral immunizing dose of a coccidial vaccine (CocciVac®, Sterwin Laboratories) was given to birds in treatments 2, 4, 6, and 8 on day 0. Birds in treatments 1, 3, 5, and 7 received orally an equal volume of saline at that time. All birds were fed the same feed and water ad libitum subsequent to day 2 after hatching. At day 14, birds in treatments 3, 4, 7, and 8 were administered a very high dose of coccidia (100x/100g BW of CocciVac®), enough to affect the performance of both naive and immunized birds.

Figure 3:
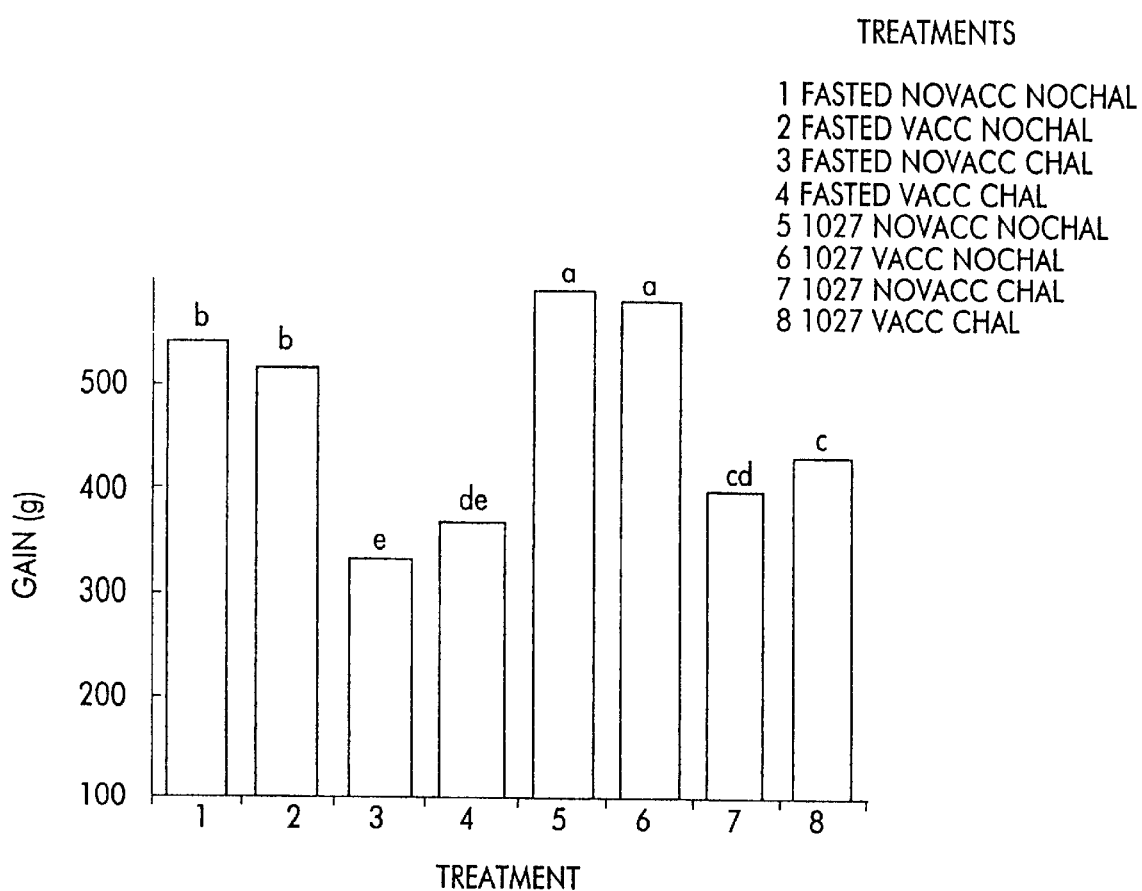
FIG. 3 is a bar graph depicting the results of Example 14.

FIG. 3 shows the cumulative gain of these birds at day 21. Compared to fasting, feeding the present high moisture material was associated with significantly higher gain in the non-vaccinated, non-challenged birds (treatment 1 vs. treatment 5), the vaccinated, non-challenged birds (treatment 2 vs. treatment 6), the non-vaccinated, challenged birds (treatment 3 vs. treatment 7), and the vaccinated, challenged birds (treatment 4 vs. treatment 8). Thus, feeding the high moisture material not only improved the ability of the non-vaccinated birds to resist the disease challenge, but also resulted in a superior performance of the vaccinated, challenged birds (treatment 8) when compared to their fasted controls (treatment 4).

These data demonstrate that feeding the high moisture solid to hatchling birds improved the general performance of the birds and their ability to respond to a disease challenge as exemplified by the performance of each of the groups receiving the high moisture material compared to its fasted control.

EXAMPLE 15

This example shows the results of an experiment in which chickens were fed high moisture material as the sole source of nutrition and hydration for the first two days of the experiment. During these two days, the birds were also variously administered adjuvants consisting of (as a percent of dry matter) muramyl dipeptide (0.015%), mannan (0.06%), killed yeast cells (0.15%), killed bacteria (*Propionibacterium acnes;* 0.03%), saponin (0.3%), levamisole (0.005%), and vitamins A (0.0001%) and E (1.5%), or saline (0.01%). All birds were given a common diet following this initial two day treatment period, and were orally vaccinated with CocciVac® coccidial vaccine on day 0 following the manufacturer's instructions.

Figure 4:
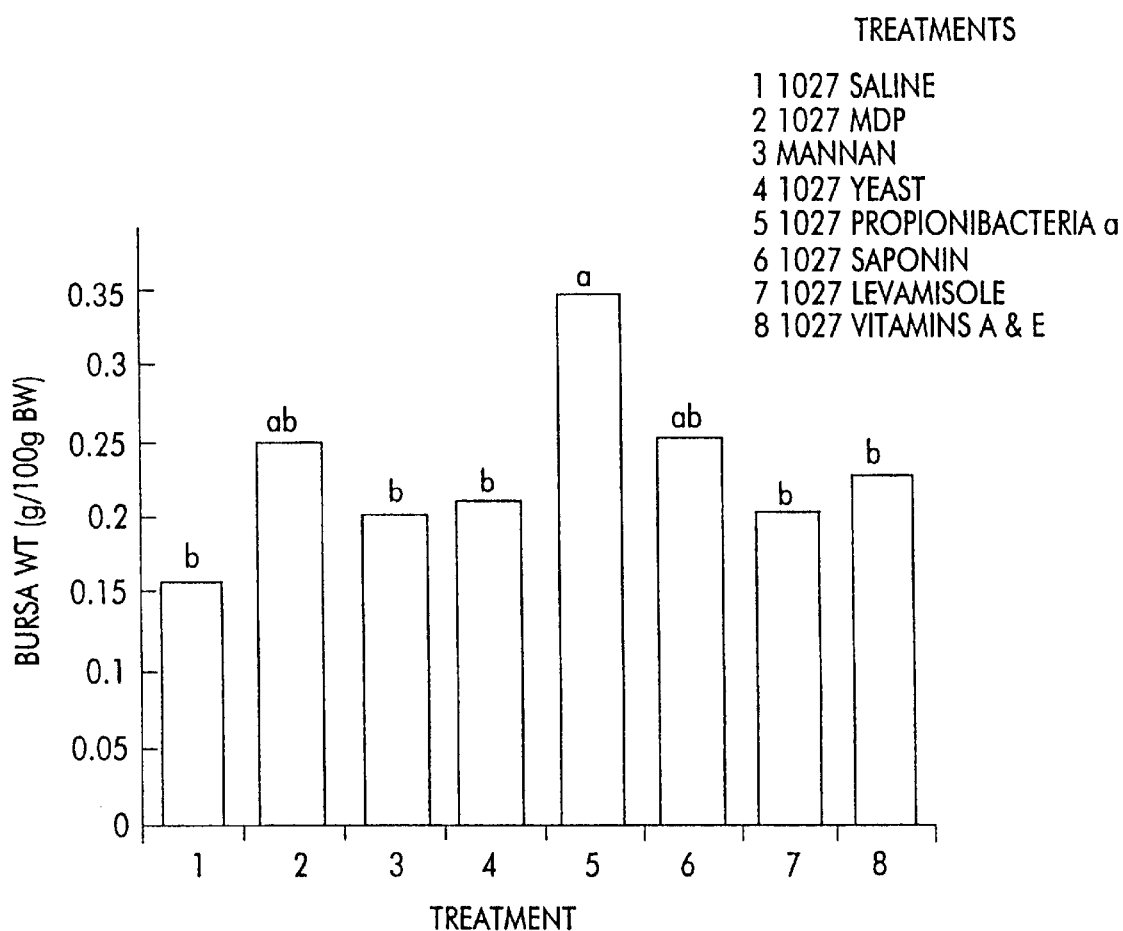
FIG. 4 is a bar graph depicting the results of Example 15.

The data in FIG. 4 show the effect of the various adjuvants on bursa weight as a percent of body weight on day 7. Clearly, several of the adjuvants were associated with a heavier relative bursa weight than in birds fed the high moisture material (designated 1027) alone. Since heavier relative bursa weight is associated with disease resistance, these data suggest that the addition of an adjuvant to the high moisture material, in association with vaccination, may improve the ability of birds to resist pathogen and other stress.

EXAMPLE 16

This example demonstrates the effect of the same adjuvants, in the same amounts, used in Example 15 on the amount of IgA in the bile of chickens, 21 days after vaccine and adjuvants were orally administered. IgA is the antibody class associated with resistance to diseases which attack the intestinal mucosa, such as coccidiosis.

Figure 5:
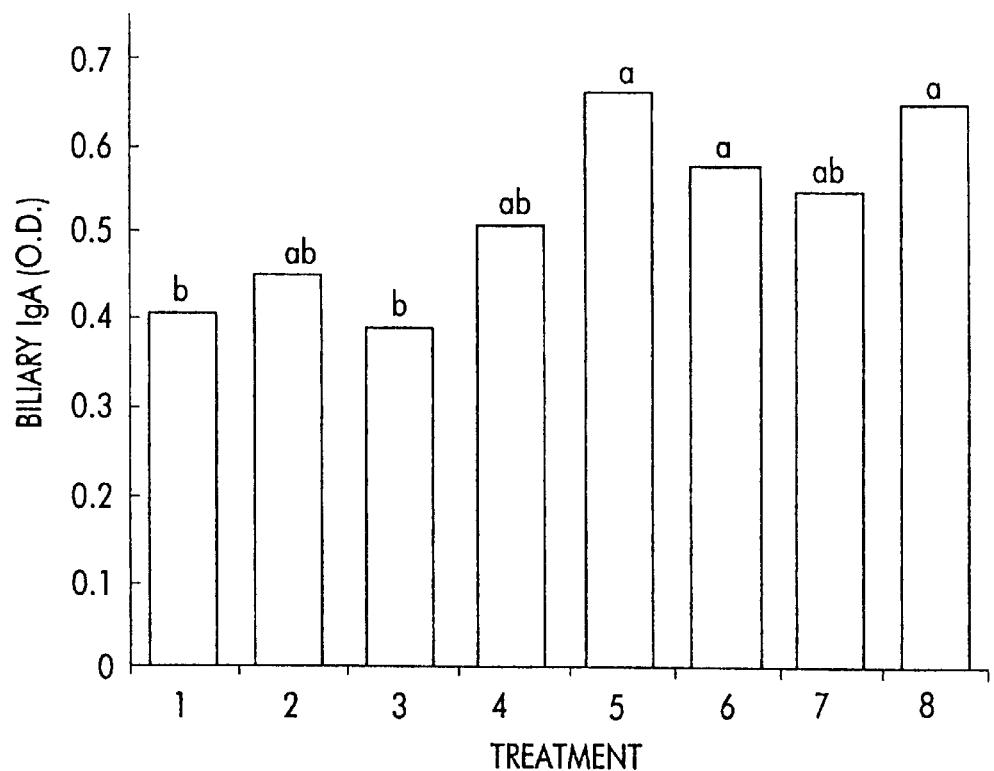
FIG. 5 is a bar graph depicting the results of Example 16.

The data presented in FIG. 5 were obtained by indirect enzyme linked immunosorbent assay (ELISA) using monoclonal mouse anti-chicken IgA as the first antibody, polyclonal goat anti-chicken IgA as the second antibody, and biotin-conjugated anti-goat immunoglobulin for detection. Samples were read on an automated ELISA plate reader, and are corrected for differences in dilution. The data demonstrate that the adjuvants contained in the high moisture material (1027) were active when administered orally, and stimulated the mucosal immune system specifically and differentially. Some, for example treatment 5 (killed *Propionibacterium acnes*), resulted in significantly higher biliary IgA content 21 days after administration of the high moisture material with the adjuvant and vaccine.

These results suggest that the high moisture material of the present invention can be used for oral delivery of adjuvants effective in stimulating the mucosal immune system in poultry. This can result in stimulation of the production of antibodies specific to, or associated with, the mucosal immune system, including the gut, respiratory system, genital-urinary system, reproductive system, and lacrimal system. This can also include stimulation of lymphocytes or cytokines characteristic of cell-mediated immunity.

EXAMPLE 17

A series of experiments was performed in chicken hatchlings in which the high moisture material (designated "1027" in FIG. 6) was administered with or without an adjuvant for two days after hatching, following which half of the birds were challenged with an oral dose of coccidial oocysts (CocciVac® used at 100 times the vaccinating dose) two weeks later. Unchallenged birds given either the high moisture material (1027) or high moisture material containing vitamin A (0.015% of dry matter) and vitamin E (0.27% of dry matter) (1027AE) were used as controls.

Figure 6:
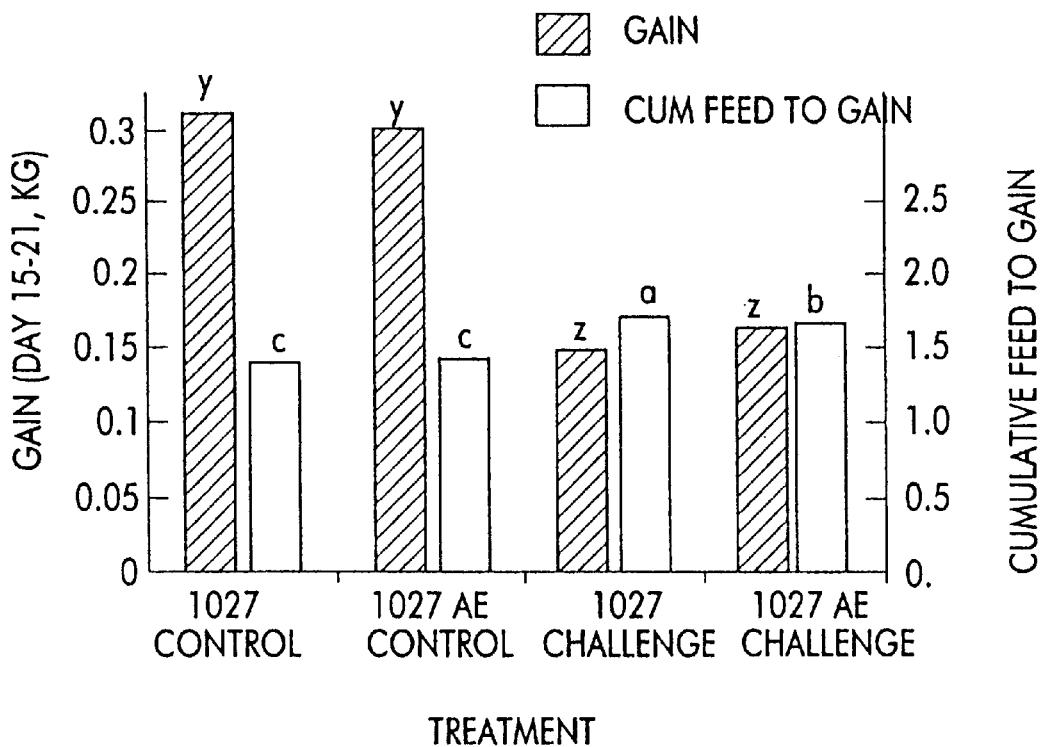
FIG. 6 is a bar graph depicting the results of Example 17.

The data in FIG. 6 present the results of this study, designed to evaluate the effects of vitamins A and E as adjuvants when given in the high moisture material over a two day period after hatching. Gain and feed efficiencies of unchallenged controls were the same 21 days after either 1027 or 1027AE treatment (the first two groups of bars). Performance of birds given coccidial challenge at day 15 is compared with that of control birds. It is clear that the challenge affected both gain and feed efficiency. However, the gain of the birds given 1027 and then challenged with coccidia is less than that in birds given 1027AE and challenged with coccidia. In addition, the feed conversion is poorer for the birds given plain 1027 than those treated with 1027 plus adjuvant and subsequently challenged. It appears that the presence of vitamins A and E in the high moisture material resulted in birds better able to withstand an oral immune stress (coccidial challenge) two weeks later.

EXAMPLE 18

Figure 7:
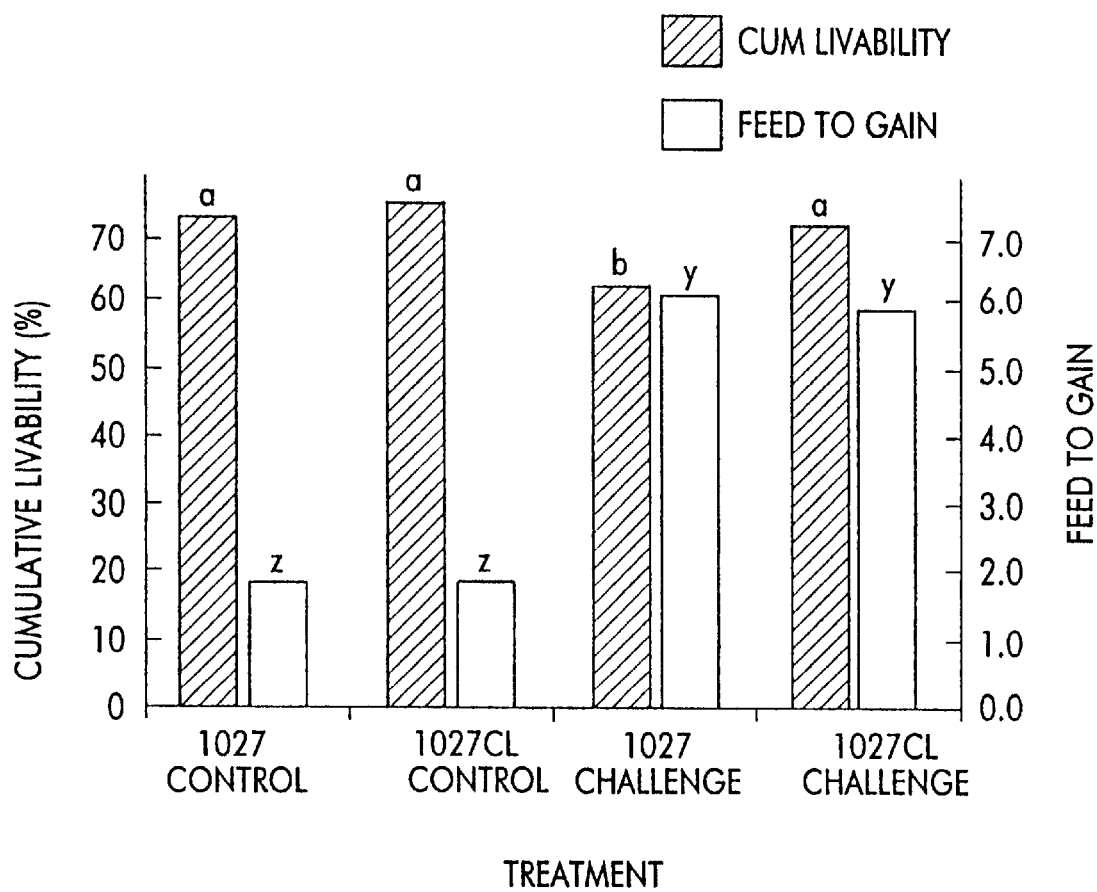
FIG. 7 is a bar graph depicting the results of Example 18.

Another example of the effects of an adjuvant is shown in FIG. 7. In this experiment, the performance of birds fed the high moisture material containing the adjuvants Concanavalin A (0.001% of dry matter) and levamisole (0.0005% of dry matter) (designated 1027CL) was compared with that of birds fed the high moisture material alone (1027). Concanavalin A and levamisole are thought to be specifically stimulatory for T-lymphocytes. As shown in Example 16, levamisole resulted in higher day 21 biliary IgA levels when given individually. In this experiment, chicken hatchlings were challenged with a coccidial stress on day 14 after administration of the high moisture material. Unchallenged birds given the high moisture material alone (1027) or high moisture material containing Concanavalin A and levamisole (1027CL) served as controls.

The data in FIG. 7 show that the presence of the adjuvants in the high moisture material (1027CL) administered on days 0 and 1 was associated with a significantly higher cumulative livability following coccidial challenge and a numerically superior feed to gain ratio during the 7 day period immediately following challenge than in birds fed the high moisture material (1027) alone. The two treatments resulted in no differences between the unchallenged control groups. As in previous Example 17, the birds which exhibited a benefit from Concanavlin A and levamisole were not previously exposed to a coccidial vaccine, but were naive at challenge on day 14.

EXAMPLE 19

In this experiment, chicken hatchlings were given killed bacterial cells of Propionibacterium spp (0.06% of dry matter) and Salmonella spp (0.06% of dry matter). As shown in Examples 15 and 16, an oral dose of killed Propionibacterium in birds vaccinated for coccidiosis results in both higher relative bursal weight and biliary IgA levels than in birds given the high moisture material alone. Similar results were observed with killed Salmonella (data not shown).

In this example, killed cells of both bacteria were administered in high moisture material on days 0 and 1 of the study. In addition, half of the birds were given an immunizing dose of CocciVac® on days 0 and 1, and a boost dose was given on day 7 (vaccinated). Vaccination in the presence of the adjuvants was associated with poorer day 14 performance, presumably due to the strong immune response, and the data were covaried for 14 day body weight in FIG. 8. All birds were challenged with coccidia on day 14.

Figure 8:
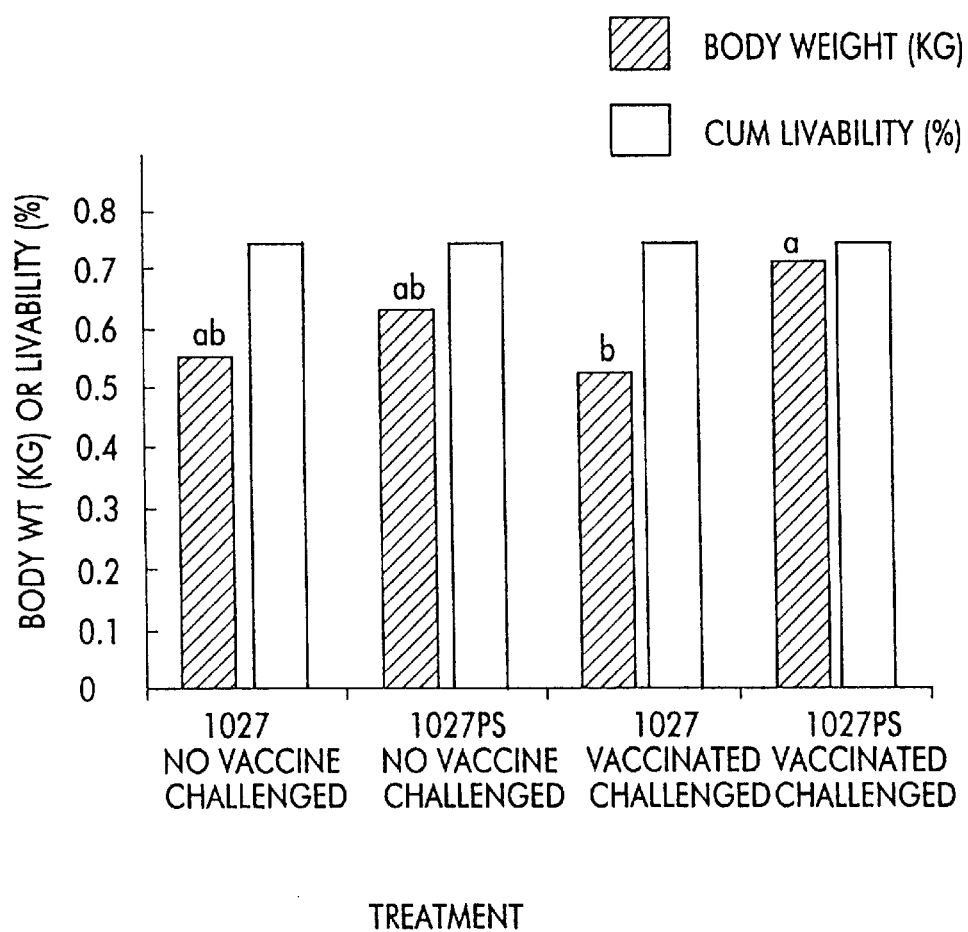
FIG. 8 is a bar graph depicting the results of Example 19.

The data shown in FIG. 8 indicate that the presence of the adjuvants was associated with improved body weight following challenge in both control and vaccinated birds. In the case of birds vaccinated before challenge, the presence of the adjuvant resulted in significantly higher body weights following challenge, indicating an improved response to the vaccine when administered in association with the oral adjuvant given in the 1027 high moisture material. Livability was not affected by any of the treatments in this experiment.

EXAMPLE 20

This example demonstrates the effect of texture and color on the ingestion of the high moisture material by hatchling turkeys. The texture agent used was millet. Turkey poults were offered colored and textured high moisture material for a period of approximately 12 hours.

Figure 9:
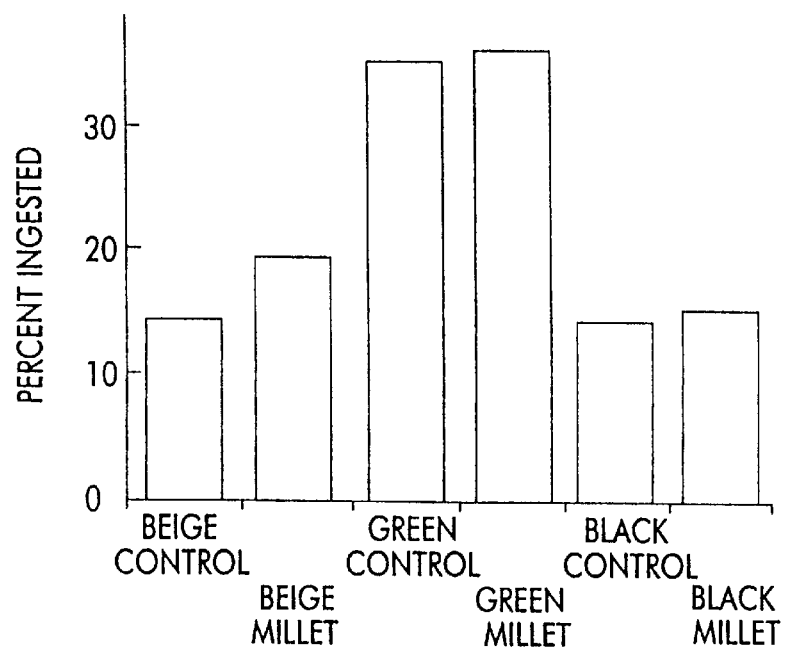
FIG. 9 is a bar graph depicting the results of Example 20.

As shown in FIG. 9, both the appearance and texture of the high moisture material influences ingestion by the birds.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What is claimed is:

1. A process for enhancing the health, livability, cumulative weight gain, or feed conversion efficiency of poultry, the process comprising making available to the poultry before the poultry is offered dry food ad libitum a high moisture material containing at least about 20% by weight water, at least 8% by weight digestible carbohydrates, and at least 7% by weight of an amino acid source, based upon the weight of the high moisture material, and an additive selected from the group consisting of a coloring agent, an adjuvant, a palatability modifier, and a combination thereof.

2. The process of claim 1, wherein the coloring agent is red, blue, green, blue-green, black, or beige.

3. The process of claim 1, wherein the palatability modifier is selected from the group consisting of grit, oyster shell, whole seeds, or grains.

4. The process of claim 1, wherein the adjuvant is selected from the group consisting of material obtained from a microorganism; a virus; a lectin; a polysaccharide; an oil emulsion; a peptide, polypeptide, or protein; and a nucleic acid.

5. The process of claim 4, wherein the material obtained from a microorganism is selected from the group consisting of a bacterial lysate, a trehalose 6,6-diester, a synthetic analogue of a trehalose 6,6-diester, muramyl dipeptide, a synthetic analogue of muramyl dipeptide, an L-seryl derivative of muramyl dipeptide, an L-valyl derivative of muramyl dipeptide, killed bacteria, Nocardia water soluble mitogen, Staphylococcus cell wall components, bestatin, killed yeast, zymosan, glucan, lentanin, an endotoxin, an enterotoxin, a bacterial cell wall peptidoglycan, and a bacterial ribonucleoprotein.

6. The process of claim 5, wherein the bacterial lysate is prepared from a bacterium of the genus Haemophilus, Diplococcus, or Neisseria.

7. The process of claim 5, wherein the killed bacteria are selected from the group consisting of killed Escherichia spp, Clostridia spp, Salmonella spp, Lactobacillus spp, Streptococcus spp, Bacillus Calmette-Guerin, Mycobacterium spp, Bordetella spp, Klebsiella spp, Brucella spp, Propionibacterium spp, Pasteurella spp, and Nocardia spp.

8. The process of claim 5, wherein the killed yeast are selected from the group consisting of killed Saccharomyces spp and Candida spp.

9. The process of claim 4, wherein the virus is selected from the group consisting of an Avipoxvirus and a Parapoxvirus.

10. The process of claim 4, wherein the lectin is selected from the group consisting of concanavalin A, pokeweed mitogen, and phytohemagglutinin.

11. The process of claim 4, wherein the polysaccharide is selected from the group consisting of a mannan, carrageenan, iota carrageenan, a hemicellulose, a levan, agar, tapioca, a dextran, a dextrin, and a lipopolysaccharide.

12. The process of claim 4, wherein the oil emulsion comprises an oil selected from the group consisting of mineral oil, peanut oil, and sesame oil.

13. The process of claim 4, wherein the peptide, polypeptide, or protein is selected from the group consisting of an interferon, an interferon inducer, a cytokine, a thymic hormone, a protease inhibitor, a chemotactic factor, tuftsin, and serum albumin.

14. The process of claim 4, wherein the nucleic acid is selected from the group consisting of a nucleic acid digest, a double stranded complementary RNA homopolymer, and immune RNA.

15. The process of claim 1, wherein the adjuvant is selected from the group consisting of a saponin, tiabenedezole, tylorone, statolon, maleic anhydride-divinyl ether, a pyran copolymer, amphotericin B, a liposome, silica, calcium phosphate, glycerol, betaine, protodyne, cyanidanol, imuthiol, picibanil, isoprinosine, lentinan, azimexon, a lecithin, levamisole, a retinol, a tocopherol, an antioxidant, an aluminum salt, aluminum hydroxide, and aluminum oxide.

16. The process of claim 1, wherein the coloring agent is blue-green.

17. A process for enhancing the resistance of poultry to a disease challenge or other stress, the process comprising making available to the poultry before the poultry is offered dry food ad libitum a high moisture material containing:

between about 50% and 80% by weight water;

at least about 10% by weight carbohydrate; and a nitrogen-containing member selected from the group consisting of protein, amino acids, amino acid precursors, amino acid analogs, and combinations thereof;

wherein the ratio of carbohydrate to the nitrogen-containing member is in the range between about 1:1 and about 3:1.

18. The process of claim 17, wherein the high moisture material contains:

between about 50% and about 80% by weight water;

at least about 10% by weight carbohydrate; and a member selected from the group consisting of:

at least about 5% by weight protein, at least about 7% by weight amino acids, amino acid precursors, amino acid analogs, or a combination thereof, a combination of at least about 5% by weight protein and at least about 5% by weight amino acids, amino acid precursors, amino acid analogs, or a combination thereof, a combination of at least about 10% by weight protein, amino acids, amino acid precursors, and amino acid analogs, and at least about 10% by weight protein.

19. The process of claim 17, further comprising administering a vaccine to the poultry.

20. The process of claim 17, wherein the high moisture material contains a blue-green coloring agent.

21. A process for enhancing the resistance of poultry to a disease challenge or other stress, the process comprising feeding a high moisture material containing:
- an adjuvant;
- between about 50% and 80% by weight water;
- at least about 10% by weight carbohydrate; and
- a nitrogen-containing member selected from the group consisting of protein, amino acids, amino acid precursors, amino acid analogs, and combinations thereof;
- wherein the ratio of carbohydrate to the nitrogen-containing member is in the range between about 1:1 and about 3:1,
- to the poultry before the poultry is offered dry food ad libitum.

22. The process of claim 21, wherein the high moisture material contains:
- between about 50% and about 80% by weight water;
- at least about 10% by weight carbohydrate;
- a member selected from the group consisting of:
  - at least about 5% by weight protein,
  - at least about 7% by weight amino acids, amino acid precursors, amino acid analogs, or a combination thereof,
  - a combination of at least about 5% by weight protein and at least about 5% by weight amino acids, amino acid precursors, amino acid analogs, or a combination thereof,
  - a combination of at least about 10% by weight protein, amino acids, amino acid precursors, and amino acid analogs, and
  - at least about 100% by weight protein.

23. The process of claim 21, further comprising administering a vaccine to the poultry.

24. The process of claim 21, wherein the adjuvant is selected from the group consisting of material obtained from a microorganism; a virus; a lectin; a polysaccharide; an oil emulsion; a peptide, polypeptide, or protein; and a nucleic acid.

25. The process of claim 24, wherein the material obtained from a microorganism is selected from the group consisting of a bacterial lysate, a trehalose 6,6-diester, a synthetic analogue of a trehalose 6,6-diester, muramyl dipeptide, a synthetic analogue of muramyl dipeptide, an L-seryl derivative of muramyl dipeptide, an L-valyl derivative of muramyl dipeptide, killed bacteria, Nocardia water soluble mitogen, Staphylococcus cell wall components, bestatin, killed yeast, zymosan, glucan, lentanin, an endotoxin, an enterotoxin, a bacterial cell wall peptidoglycan, and a bacterial ribonucleoprotein.

26. The process of claim 25, wherein the bacteria lysate is prepared from a bacterium of the genus Haemophilus, Diplococcus, or Neisseria.

27. The process of claim 25, wherein the killed bacteria are selected from the group consisting of killed Escherichia spp, Clostridia spp, Salmonella spp, Lactobacillus spp, Streptococcus spp, Bacillus Calmette-Guerin, Mycobacterium spp, Bordetella spp, Klebsiella spp, Brucella spp, Propionibacterium spp, Pasteurella spp, and Nocardia spp.

28. The process of claim 25, wherein the killed yeast are selected from the group consisting of killed Saccharomyces spp and Candida spp.

29. The process of claim 24, wherein the virus is selected from the group consisting of an Avipoxvirus and a Parapoxvirus.

30. The process of claim 24, wherein the lectin is selected from the group consisting of concanavalin A, pokeweed mitogen, and phytohemagglutinin.

31. The process of claim 24, wherein the polysaccharide is selected from the group consisting of a mannan, carrageenan, iota carrageenan, a hemicellulose, a levan, agar, tapioca, a dextran, a dextrin, and a lipopolysaccharide.

32. The process of claim 24, wherein the oil emulsion comprises an oil selected from the group consisting of mineral oil, peanut oil, and sesame oil.

33. The process of claim 24, wherein the peptide, polypeptide, or protein is selected from the group consisting of an interferon, an interferon inducer, a cytokine, a thymic hormone, a protease inhibitor, a chemotactic factor, tuftsin, and serum albumin.

34. The process of claim 24, wherein the nucleic acid is selected from the group consisting of a nucleic acid digest, a double stranded complementary RNA homopolymer, and immune RNA.

35. The process of claim 21, wherein the adjuvant is selected from the group consisting of a saponin, tiabenedezole, tylorone, statolon, maleic anhydride-divinyl ether, a pyran copolymer, amphotericin B, a liposome, silica, calcium phosphate, glycerol betaine, protodyne, cyanidanol, imuthiol, picibanil, isoprinosine lentinan, azimexon, a lecithin, levamisole, a retinol, a tocopherol, an antioxidant, an aluminum salt, aluminum hydroxide, and aluminum oxide.

36. A process for stimulating the mucosal, immune system in poultry, the process comprising feeding a high moisture material containing:
- an adjuvant;
- between about 50% and 80% by weight water;
- at least about 10% by weight carbohydrate; and
- a nitrogen-containing member selected from the group consisting of protein, amino acids, amino acid precursors, amino acid analogs, and combinations thereof;
- wherein the ratio of carbohydrate to the nitrogen-containing member is in the range between about 1:1 and about 3:1,
- to the poultry before the poultry is offered dry food ad libitum.

37. The process of claim 36, further comprising administering a vaccine to the poultry.

38. A high moisture material for stimulating the growth of newly hatched poultry comprising, based on the weight of the high moisture material, at least about 20% by weight water, at least 8% by weight digestible carbohydrates, at least 7% by weight of an amino acid source, and no more than 5% by weight fat,
- wherein the water retention capacity of the high moisture material is such that it does not release free water in an amount sufficient to dampen poultry hatchlings as a consequence of their coming into contact with it, and
- wherein the high moisture material contains a blue-green coloring agent.

39. The high moisture material of claim 38, which is in the form of an extrudate.

40. A process for hatching poultry eggs, comprising:
(a) placing a set of poultry eggs in an incubator until the poultry hatches from the eggs, (b) placing the hatchlings in a shipping container for shipment to a remote location, (c) shipping the hatchlings in the shipping container to a remote location, and (d) making available to the hatchlings before the hatchlings are allowed to eat dry food ad libitum a high moisture material by placing the high moisture material along with the hatchlings in the shipping container, the high moisture material containing at least about 20% by weight water, at least 8% by weight digestible carbohydrates, and at least 7% by weight of an amino acid source, based upon the weight of the high moisture material, wherein the high-moisture material contains a blue-green coloring agent.

* * * * *

UNITED STATES PATENT AND TRADEMARK OFFICE
CERTIFICATE OF CORRECTION

PATENT NO.   : 5,976,580
DATED        : November 2, 1999
INVENTOR(S)  : Francis J. Ivey It is certified that error appears in the above-identified patent and that said Letters Patent is hereby corrected as shown below:

<u>Column 27,</u>
Line 37, "100%" should read -- 10% --.

Signed and Sealed this

Twentieth Day of August, 2002

Attest:

Attesting Officer

JAMES E. ROGAN
Director of the United States Patent and Trademark Office